(12) United States Patent
Ma

(10) Patent No.: US 11,384,156 B2
(45) Date of Patent: Jul. 12, 2022

(54) ADOPTIVE T-CELL THERAPY USING EMPD-SPECIFIC CHIMERIC ANTIGEN RECEPTORS FOR TREATING IGE-MEDIATED ALLERGIC DISEASES

(71) Applicant: THE NEMOURS FOUNDATION, Jacksonville, FL (US)

(72) Inventor: Zhengyu Ma, Garnet Valley, PA (US)

(73) Assignee: THE NEMOURS FOUNDATION, Jacksonville, FL (US)

( * ) Notice: Subject to any disclaimer, the term of this patent is extended or adjusted under 35 U.S.C. 154(b) by 0 days.

(21) Appl. No.: 15/651,264

(22) Filed: Jul. 17, 2017

(65) Prior Publication Data

US 2018/0022826 A1  Jan. 25, 2018

Related U.S. Application Data

(60) Provisional application No. 62/366,328, filed on Jul. 25, 2016.

(51) Int. Cl.
| | | |
|---|---|---|
| *A61K 35/17* | (2015.01) | |
| *A61K 39/00* | (2006.01) | |
| *C07K 16/42* | (2006.01) | |
| *G02F 1/09* | (2006.01) | |
| *A61P 37/08* | (2006.01) | |
| *C07K 16/28* | (2006.01) | |
| *C07K 16/00* | (2006.01) | |

(52) U.S. Cl.
CPC .......... *C07K 16/4291* (2013.01); *A61P 37/08* (2018.01); *C07K 16/28* (2013.01); *G02F 1/09* (2013.01); *A61K 2039/505* (2013.01); *C07K 16/00* (2013.01); *C07K 2317/24* (2013.01); *C07K 2317/34* (2013.01); *C07K 2317/622* (2013.01); *C07K 2317/73* (2013.01); *C07K 2319/03* (2013.01); *C07K 2319/33* (2013.01)

(58) Field of Classification Search
CPC .......... A61K 35/17; A61K 2039/505
See application file for complete search history.

(56) References Cited

U.S. PATENT DOCUMENTS

| | | | |
|---|---|---|---|
| 8,211,422 B2 | 7/2012 | Eshhar et al. | |
| 8,460,664 B2 | 6/2013 | Chang et al. | |
| 8,974,794 B2 * | 3/2015 | Chang ................ | C07K 16/4291 424/185.1 |
| 10,195,272 B2 * | 2/2019 | Ma ..................... | A61K 39/3955 |
| 2009/0010924 A1 | 1/2009 | Wu et al. | |
| 2013/0287748 A1 | 10/2013 | June et al. | |
| 2014/0106499 A1 | 4/2014 | June et al. | |
| 2014/0286973 A1 | 9/2014 | Powerll, Jr. | |
| 2015/0368342 A1 | 12/2015 | Wu et al. | |
| 2016/0096892 A1 | 4/2016 | Brogdon et al. | |
| 2016/0145337 A1 | 5/2016 | Galetto et al. | |
| 2018/0162939 A1 * | 6/2018 | Ma ........................... | C12N 5/10 |

FOREIGN PATENT DOCUMENTS

| | | |
|---|---|---|
| WO | WO-2013/126712 A1 | 8/2013 |
| WO | WO-2014/039523 A1 | 3/2014 |

OTHER PUBLICATIONS

Bridgeman et al. (J.Immunol. Jun. 15, 2010; 184 (12): 6938-49).*
Ma et al. (Prostate. Sep. 15, 2004; 61 (1): 12-25).*
Hudecek et al. (Clin. Cancer Res. Jun. 15, 2013; 19 (12): 3153-64).*
Lustgarten et al. (Eur. J. Immunol. Oct. 1995; 25 (10): 2985-91).*
Kochenderfer et al. (Blood. Nov. 18, 2010; 116 (20): 4099-102).*
Brightbill et al. (J. Clin. Invest. Jun. 2010; 120 (6): 2218-29).*
Feichtner et al. (J. Immunol. Apr. 15, 2008; 180 (8): 5499-505).*
Love et al. (Cold Spring Harb. Perspect. Biol. 2010; 2: a002485; pp. 1-12).*
Barrow et al. (Eur. J. Immunol. 2006; 36: 1646-53).*
Ivashkiv (Sci. Signal. Apr. 19, 2011; 4 (169): pe20; pp. 1-6).*
Wang et al. (J. Cell Sci. 2011; 124: 2702-10).*
Dotti et al. (Immunol. Rev. 2014; 257 (1): 10.1111/imr.12131; pp. 1-35).*
James (Sci. Signal. May 22, 2018; 11 (531): eaan1088; pp. 1-23).*
Stoiber et al. (Cells. May 2019; 8 (5): 472; pp. 1-26).*
Hennecke et al. (J. Biol. Chem. 1993; 268: 26607-12).*
Hook et al. (Mol. Immunol. Jun. 1991; 28 (6): 631-9).*
Ward et al. (Front. Immunol. Oct. 10, 2018; 9: 2231; pp. 1-11).*
U.S. Appl. No. 15/058,286, filed Mar. 2, 2016, Zhengyu Ma.
U.S. Appl. No. 15/084,192, filed Mar. 29, 2016, Zhengyu Ma.
Brightbill H.D., et al., "Antibodies specific for a segment of human membrane IgE deplete IgE-producing B cells in humanized mice", *Journal of Clinical Investigation*, Jun. 6, 2010;120(6):2218-29. doi: 10.1172/JCI40141. Epub May 10, 2010.
Harris, J.M., "A randomized trial of the efficacy and safety of quilizumab in adults with inadequately controlled allergic asthma," *Respiratory Research*, Mar. 2016., 18;17:29. doi: 10.1186/S12931-016-0347-2.
Wu, Chia-Yung, et al., "Remote control of therapeutic T cells through a small molecule-gated chimeric receptor," *Science* 350(6258): aab4077-1 to 10 (2015) http://science.sciencemag.org/content/350/6258/aab4077.
Feichtner, Stefan, et al., "Targeting the Extracellular Membrane-Proximal Domain of Membrane-Bound IgE by Passive Immunization Blocks IgE Synthesis in Vivo1," *J. Immunology*. 180(8); 5499-5505 (2008) https://www.ncbi.nlm.nih.gov/pmc/articles/PMC2959155/.

(Continued)

*Primary Examiner* — Stephen L Rawlings
(74) *Attorney, Agent, or Firm* — Faegre Drinker Biddle & Reath LLP

(57) ABSTRACT

A chimeric antigen receptor specific for the extracellular membrane-proximal domain (EMPD) of membrane-bound IgE (mIgE) is provided. The EMPD-specific chimeric antigen receptor comprises an extracellular ligand binding domain capable of binding EMPD, a transmembrane domain, and an intracellular domain that mediates T cell activation upon EMPD binding. Nucleic acids and vectors encoding the EMPD-specific chimeric antigen receptor are provided. T cells transduced with such vectors find use in chimeric antigen receptor-based adoptive T-cell therapy for targeting IgE-expressing B cells and treating IgE-mediated allergic diseases.

26 Claims, 9 Drawing Sheets

Specification includes a Sequence Listing.

(56) References Cited

OTHER PUBLICATIONS

Jensen, Michael, C., et al., "Design and Implementation of Adoptive Therapy with Chimeric Antigen Receptor-Modified T Cells," *Immunol. Rev.* 257(1): 127-144 (2014) https://www.ncbi.nlm.nih.gov/pubmed/24329794.

Chu, Hsing-Mao, et al., "Two potential therapeutic antibodies bind to a peptide segment of membrane-bound of IgE in different conformations," *Nature Comm.* 5(3139): 3-7 http://www.nature.com/articles/ncomms4139.

Brightbill, H.D., et al., "Antibodies specific for a segment of human membrane IgE deplete IgE-producing B cells in Humanized mice," *J. Clin. Investigation* 120(6): 2218-2229 (2010) https://www.jci.org/articles/view/40141.

Poggianella, Monica, et al., "The Extracellular Membrane-Proximal Domain of Human Membrane IgE Controls Apoptotic Signaling of the B Cell Receptor in the Mature B Cell Line A20," *J. Immunol.* 177: 3597-3605 (2016); http://www.jimmunol.org/content/jimmunol/177/6/3597.full.pdf.

Sadelain, Michel, et al., "The Basic Principles of Chimeric Antigen Receptor Design," *Cancer Discovery* 3(4): 1-11 (2013); http://cancerdiscovery.aacrjournals.org/content/candisc/3/4/388.full.pdf.

Bestango, Marco, et al., "Membrane Immunoglobulins Are Stabilized by Interchain Disulfide Bonds Occurring within the Extracellular Membrane-Proximal Domain," *Biochemistry* 40: 10686-10692 (2001); https://pubs.acs.org/doi/abs/10.1021/bi010506%2B?journalCode=bichaw.

Ma, Zhengyu, et al., "Chimeric antigen receptors based on low affinity mutants of FcεRI re-direct T cell specificity of cells expressing membrane IgE (HYP5P.321)," *J. Immunol.* 194(Supp. 124.4): (2015) http://www.jimmunol.org/content/194/1_Supplement/124.4.

* cited by examiner

FIG. 3a

```
  1 M D F Q V Q I F S F L L I S A S V I M S          Ig kappa
  1 ATGGATTTTCAGGTGCAGATTTTCAGCTTCCTGCTAATCAGTGCCTCAGTCATAATGTCC  signal pep 21 R G D I V M S Q S P S S L A V S V G E K
 61 AGAGGAGACATTGTGATGTCACAGTCTCCATCCTCCCTAGCTGTGTCAGTTGGAGAGAAG 41 V T M S C K S S Q S L L Y S S N Q K N Y
121 GTTACTATGAGCTGCAAGTCCAGTCAGAGCCTTTTATATAGTAGCAATCAAAAGAACTAC 61 L A W Y Q Q K P G Q S P K L L I Y W A S
181 TTGGCCTGGTACCAGCAGAAACCAGGGCAGTCTCCTAAACTGCTGATTTACTGGGCATCC 81 T R E S G V P D R F T G S G S G T D F T    scFv VL
241 ACTAGGGAATCTGGGGTCCCTGATCGCTTCACAGGCAGTGGATCTGGGACAGATTTCACT 101 L T I S S V K A E D L A V Y Y C Q Q Y Y
301 CTCACCATCAGCAGTGTGAAGGCTGAAGACCTGGCAGTTTATTACTGTCAGCAATATTAT 121 S Y P Y T F G G G T K L E I K R G S T S
361 AGCTATCCGTACACGTTCGGAGGGGGGACCAAGCTGGAAATAAAACGGGGGTCTACATCC 141 G S G K P G S G E G S E V Q L Q Q S G T    Linker
421 GGATCTGGGAAGCCGGGTTCTGGTGAGGGTTCGAGGTTCAGCTGCAGCAGTCTGGGACT 161 V L A R P G A S V K M S C K A S G Y S F
481 GTGCTGGCAAGGCCGGGGGCTTCCGTGAAGATGTCCTGCAAGGCTTCTGGCTACAGCTTT 181 T S H W M H W V K Q R P G Q G L E W I G
541 ACCAGCCACTGGATGCACTGGGTAAAACAGAGGCCTGGACAGGGTCTAGAATGGATTGGT 201 A I Y P G N S D T I Y N Q K F K G K A K    scFv VH
601 GCTATTTATCCTGGAAATAGTGATACTATCTACAACCAGAAGTTCAAGGGCAAGGCCAAA 221 L T A V T S A S T A Y M E L S S L T N E
661 CTGACTGCAGTCACATCCGCCAGCACTGCCTACATGGAGCTCAGCAGCCTGACAAATGAG 241 D S A V Y Y C T R W R D D N Y D Y D M D
721 GACTCTGCGGTCTATTACTGTACAAGATGGAGGGATGACAACTACGACTATGATATGGAC 261 Y W G Q G T S V T V S S A A A F V P V F
781 TACTGGGGTCAAGGAACCTCAGTCACCGTCTCCTCAGCGGCCGCATTCGTGCCGGTGTTC 281 L P A K P T T T P A P R P P T P A P T I    CD8 hinge
841 CTGCCAGCGAAGCCCACCACGACGCCAGCGCCGCGACCACCAACACCGGCGCCCACCATC 301 A S Q P L S L R P E A C R P A A G G A V
901 GCGTCGCAGCCCCTGTCCCTGCGCCCAGAGGCGTGCCGGCCAGCAGGCGGGAGGAGCAGTG 321 H T R G L D F A C D I Y I W A P L A G T    CD8 transm
961 CACACGAGGGGGCTGGACTTCGCCTGTGATATCTACATCTGGGCGCCCTTGGCCGGGACT  domain 341 C G V L L L S L V I T L Y C N H R N R S    CD8 intra
1021 TGTGGGGTCCTTCTCCTGTCACTGGTTATCACCCTTTACTGCAACCACAGGAACAGGAGT  domain
```

FIG. 3b

```
361 K  R  S  R  L  L  H  S  D  Y  M  N  M  T  P  R  R  P  G  P
1081 AAGAGGAGCAGGCTCCTGCACAGTGACTACATGAACATGACTCCCCGCCGCCCCGGGCCC

381 T  R  K  H  Y  Q  P  Y  A  P  P  R  D  F  A  A  Y  R  S  R      CD28 and
1141 ACCCGCAAGCATTACCAGCCCTATGCCCCACCACGCGACTTCGCAGCCTATCGCTCCCGT    4-1BB
                                                                     Signaling
401 F  S  V  V  K  R  G  R  K  K  L  L  Y  I  F  K  Q  P  F  M      domain
1201 TTCTCTGTTGTTAAACGGGGCAGAAAGAAGCTCCTGTATATATTCAAACAACCATTTATG 421 R  P  V  Q  T  T  Q  E  E  D  G  C  S  C  R  F  P  E  E  E
1261 AGACCAGTACAAACTACTCAAGAGGAAGATGGCTGTAGCTGCCGATTTCCAGAAGAAGAA 441 E  G  G  C  E  L  R  V  K  F  S  R  S  A  D  A  P  A  Y  Q
1321 GAAGGAGGATGTGAACTGAGAGTGAAGTTCAGCAGGAGCGCAGACGCCCCCGCGTACCAG
```
```
461 Q  G  Q  N  Q  L  Y  N  E  L  N  L  G  R  R  E  E  Y  D  V
1381 CAGGGCCAGAACCAGCTCTATAACGAGCTCAATCTAGGACGAAGAGAGGAGTACGATGTT
```
```
481 L  D  K  R  R  G  R  D  P  E  M  G  G  K  P  Q  R  R  K  N      CD3ζ
1441 TTGGACAAGAGACGTGGCCGGGACCCTGAGATGGGGGGAAAGCCGCAGAGAAGGAAGAAC    intra
                                                                     domain
501 P  Q  E  G  L  Y  N  E  L  Q  K  D  K  M  A  E  A  Y  S  E
1501 CCTCAGGAAGGCCTGTACAATGAACTGCAGAAAGATAAGATGGCGGAGGCCTACAGTGAG
```
```
521 I  G  M  K  G  E  R  R  R  G  K  G  H  D  G  L  Y  Q  G  L
1561 ATTGGGATGAAAGGCGAGCGCCGGAGGGGCAAGGGGCACGATGGCCTTTACCAGGGTCTC
```
```
541 S  T  A  T  K  D  T  Y  D  A  L  H  M  Q  A  L  P  P  R
1621 AGTACAGCCACCAAGGACACCTACGACGCCCTTCACATGCAGGCCCTGCCCCCTCGG
```

FIG. 5a

```
  1 M  D  F  Q  V  Q  I  F  S  F  L  L  I  S  A  S  V  I  M  S         Ig kappa
  1 ATGGATTTTCAGGTGCAGATTTTCAGCTTCCTGCTAATCAGTGCCTCAGTCATAATGTCC         signal
                                                                         peptide 21 R  G  D  I  V  M  S  Q  S  P  S  S  L  A  V  S  V  G  E  K
 61 AGAGGAGACATTGTGATGTCACAGTCTCCATCCTCCCTAGCTGTGTCAGTTGGAGAGAAG 41 V  T  M  S  C  K  S  S  Q  S  L  L  Y  S  S  N  Q  K  N  Y
121 GTTACTATGAGCTGCAAGTCCAGTCAGAGCCTTTTATATAGTAGCAATCAAAAGAACTAC 61 L  A  W  Y  Q  Q  K  P  G  Q  S  P  K  L  L  I  Y  W  A  S         scFv VL
181 TTGGCCTGGTACCAGCAGAAACCAGGGCAGTCTCCTAAACTGCTGATTTACTGGGCATCC 81 T  R  E  S  G  V  P  D  R  F  T  G  S  G  S  G  T  D  F  T
241 ACTAGGGAATCTGGGGTCCCTGATCGCTTCACAGGCAGTGGATCTGGGACAGATTTCACT 101 L  T  I  S  S  V  K  A  E  D  L  A  V  Y  Y  C  Q  Q  Y  Y
301 CTCACCATCAGCAGTGTGAAGGCTGAAGACCTGGCAGTTTATTACTGTCAGCAATATTAT 121 S  Y  P  W  T  F  G  G  G  T  K  L  E  I  K  R  G  S  T  S
361 AGCTATCCGTGGACGTTCGGTGGAGGCACCAAGCTGGAAATCAAACGGGGTTCTACATCT         linker 141 C  S  G  K  P  G  S  S  E  G  S  D  V  Q  L  Q  E  S  G  P
421 GGATCTGGAAAGCCGGGTTCTGGTGAGGGTTCTGATGTACAGCTTCAGGAGTCAGGACCT 161 G  L  V  K  P  S  Q  S  L  S  L  T  C  S  V  T  G  Y  S  I
481 GGCCTCGTGAAACCTTCTCAGTCTCTGTCTCTCACCTGCTCTGTCACTGGCTACTCCATC 181 T  S  G  Y  Y  W  N  W  I  R  Q  F  P  G  N  K  L  E  W  M
541 ACCAGTGGTTATTACTGGAACTGGATCCGGCAGTTTCCAGGTAACAAACTGGAATGGATG         scFv VH 201 G  S  I  S  Y  D  G  S  N  N  Y  N  P  S  L  K  N  R  I  S
601 GGCTCCATAAGCTACGACGGTAGCAATAACTACAACCCATCTCTCAAAAATCGAATCTCC 221 I  T  R  D  T  S  K  N  Q  F  F  L  K  L  N  S  V  T  T  E
661 ATCACTCGTGACACATCTAAGAACCAGTTTTTCCTGAAGTTGAATTCTGTGACTACTGAG 241 D  T  A  T  Y  Y  C  A  R  D  Y  G  G  F  D  Y  W  G  Q  G
721 GACACAGCTACATATTACTGTGCAAGAGACTACGGGGGCTTTGACTACTGGGGCCAAGGC 261 T  T  L  T  V  S  S  A  A  A  F  V  P  V  F  L  P  A  K  P
781 ACCACTCTCACAGTCTCCTCAGCGGCCGCATTCGTGCCGGTCTTCCTGCCAGCGAAGCCC 281 T  T  T  P  A  P  R  P  P  T  P  A  P  T  I  A  S  Q  P  L         CD8 hinge
841 ACCACGACGCCAGCGCCGCGACCACCAACACCGGCGCCCACCATCGCGTCGCAGCCCCTG 301 S  L  R  P  E  A  C  R  P  A  A  G  G  A  V  H  T  R  G  L
901 TCCCTGCGCCCAGAGGCGTGCCGGCCAGCAGCACGGAGGACCAGTGCACACGAGGGGGCTG 321 D  F  A  C  D  I  Y  I  W  A  P  L  A  G  T  C  G  V  L  L         CD8 transm
961 GACTTCGCCTGTGATATCTACATCTGGGCGCCCTTGGCCGGGACTTGTGGGGTCCTTCTC         domain 341 L  S  L  V  I  T  L  Y  C  N  H  R  N  R  S  K  R  S  R  L         CD8 intra
1021 CTGTCACTGGTTATCACCCTTTACTGCAACCACAGGAACAGGAGTAAGAGGAGCAGGCTC        domain
```

FIG. 5b

```
 361 L  H  S  D  Y  M  N  M  T  P  R  R  P  G  P  T  R  K  H  Y
1081 CTGCACAGTGACTACATGAACATGACTCCCCGCCGCCCCGGGCCCACCCGCAAGCATTAC

381 Q  P  Y  A  P  P  R  D  F  A  A  Y  R  S  R  F  S  V  V  K          CD28 and
1141 CAGCCCTATGCCCCACCACGCGACTTCGCAGCCTATCGCTCCCGTTTCTCTGTTGTTAAA         4-1BB
                                                                          signaling
 401 R  G  R  K  K  L  L  Y  I  F  K  Q  P  F  M  R  P  V  Q  T          domain
1201 CGGGGCAGAAAGAAGCTCCTGTATATATTCAAACAACCATTTATGAGACCAGTACAAACT 421 T  Q  E  E  D  G  C  S  C  R  F  P  E  E  E  E  G  G  C  E
1261 ACTCAAGAGGAAGATGGCTGTAGCTGCCGATTTCCAGAAGAAGAAGAAGGAGGATGTGAA 441 L  R  V  K  F  S  R  S  A  D  A  P  A  Y  Q  Q  G  Q  N  Q
1321 CTGAGAGTGAAGTTCAGCAGGAGCGCAGACGCCCCCGCGTACCAGCAGGGCCAGAACCAG 461 L  Y  N  E  L  N  L  G  R  R  E  E  Y  D  V  L  D  K  R  R
1381 CTCTATAACGAGCTCAATCTAGGACGAAGAGAGGAGTACGATGTTTTGGACAAGAGACGT 481 G  R  D  P  E  M  G  G  K  P  Q  R  R  K  N  P  Q  E  G  L         CD3ζ
1441 GGCCGGGACCCTGAGATGGGGGGAAAGCCGCAGAGAAGGAAGAACCCTCAGGAAGGCCTG         intra-
                                                                         domain
 501 Y  N  E  L  Q  K  D  K  M  A  E  A  Y  S  E  I  G  M  K  G
1501 TACAATGAACTGCAGAAAGATAAGATGGCGGAGGCCTACAGTGAGATTGGGATGAAAGGC 521 E  R  R  R  G  K  G  H  D  G  L  Y  Q  G  L  S  T  A  T  K
1561 GAGCGCCGGAGGGGCAAGGGGCACGATGGCCTTTACCAGGGTCTCAGTACAGCCACCAAG 541 D  T  Y  D  A  L  H  M  Q  A  L  P  P  R
1621 GACACCTACGACGCCCTTCACATGCAGGCCCTGCCCCCTCGG
```

FIG. 6a

```
  1  M  D  F  Q  V  Q  I  F  S  F  L  L  I  S  A  S  V  I  M  S         Ig kappa
  1  ATGGATTTTCAGGTGCAGATTTTCAGCTTCCTGCTAATCAGTGCCTCAGTCATAATGTCC         Signal
                                                                         peptide 21  R  G  D  V  V  M  T  Q  T  P  L  T  L  S  V  T  I  G  Q  P
 61  ACAGGAGATGTTGTGATGACCCAGACTCCACTCACTTTGTCGGTTACCATTGGACAACCA 41  A  S  I  S  C  K  S  S  Q  S  L  L  Y  S  D  G  K  T  Y  L
121  GCCTCCATCTCTTGCAAGTCAAGTCAGAGCCTCTTATATAGTGATGGAAAGACATATTTG 61  N  W  L  L  Q  R  P  G  Q  S  P  K  R  L  I  Y  L  V  S  K         scFv VL
181  AATTGGTTGTTACAGAGGCCAGGCCAGTCTCCAAAGCGCCTAATCTATCTGGTGTCTAAA 81  L  D  S  G  V  P  D  R  F  T  G  S  G  S  G  T  D  F  T  L
241  CTGGACTCTGGAGTCCCTGACAGGTTCACTGGCAGTGGATCAGGGACAGATTTCACACTG 101  K  I  S  R  V  E  A  E  D  L  G  V  Y  Y  C  W  Q  G  T  H
301  AAAATCAGCAGAGTGGAGGCTGAGGATTTGGGAGTTTATTATTGCTGGCAAGGTACACAT 121  F  P  R  T  F  G  G  G  T  K  L  E  I  K  R  G  S  T  S  G
361  TTTCCTCGGACGTTCGGTGGAGGCACCAAGCTGGAAATCAAACGGGGGTCTACATCTGGA         Linker 141  S  G  K  P  G  S  G  E  G  S  D  V  Q  L  Q  E  S  G  P  G
421  TCTGGGAAGCCCGGGTCTGGTGAGGGTTCTGATGTGCAGCTTCAGGAGTCAGGACCTGGC 161  L  V  K  P  S  Q  S  L  S  L  T  C  T  V  T  G  Y  S  I  T
481  CTGGTGAAACCTTCTCAGTCTCTGTCCCTCACCTGCACTGTCACTGGCTACTCAATCACC 181  S  D  Y  A  W  N  W  I  R  Q  F  P  R  N  K  L  E  W  M  G
541  AGTGATTATGCCTGGAACTGGATCCGGCAGTTTCCAAGAAACAAACTGGAGTGGATGGGC 201  Y  I  S  Y  S  G  R  N  S  Y  N  P  S  L  K  S  R  I  S  I         scFv VH
601  TACATAAGCTACAGTGGTAGGAATAGCTACAACCCATCTCTCAAAAGTCGAATCTCTATC 221  T  R  D  T  S  K  N  Q  F  F  L  Q  L  N  S  V  T  T  E  D
661  ACTCGAGACACATCCAAGAACCAGTTCTTCCTGCAGTTGAATTCTGTGACTACTGAGGAC 241  T  A  T  Y  Y  C  A  R  W  G  D  F  D  V  W  G  A  G  T  T
721  ACAGCCACATATTACTGTGCAAGATGGGGGGACTTCGATGTCTGGGGCGCAGGGACCACG 261  V  T  V  S  S  A  A  A  F  V  P  V  F  L  P  A  K  P  T  T
781  GTCACCGTCTCCTCAGCGGCCGCATTCGTGCCGGTCTTCCTGCCAGCGAAGCCCACCACG 281  T  P  A  P  R  P  P  T  P  A  P  T  I  A  S  Q  P  L  S  L         CD8 hinge
841  ACGCCAGCGCCGCGACCACCAACACCGGCGCCCACCATCGCGTCGCAGCCCCTGTCCCTG 301  R  P  E  A  C  R  P  A  A  G  G  A  V  H  T  R  G  L  D  F
901  CGCCCAGAGGCGTGCCGGCCAGCGGCGGGGGGCGCAGTGCACACGAGGGGGCTGGACTTC
```

FIG. 6b

```
321 A  C  D  I  Y  I  W  A  P  L  A  G  T  C  G  V  L  L  L  S       CD8 Intra.
961 GCCTGTGATATCTACATCTGGGCGCCCTTGGCCGGGACTTGTGGGGTCCTTCTCCTGTCA      domain 341 L  V  I  T  L  Y  C  N  H  R  N  R  S  K  R  S  R  L  L  H       CD8 transm
1021 CTGGTTATCACCCTTTACTGCAACCACAGGAACAGGAGTAAGAGGAGCAGGCTCCTGCAC      domain 361 S  D  Y  M  N  M  T  P  R  R  P  G  P  T  R  K  H  Y  Q  P
1081 AGTGACTACATGAACATGACTCCCCGCCGCCCCGGGCCCACCCGCAAGCATTACCAGCCC 381 Y  A  P  P  R  D  F  A  A  Y  R  S  R  F  S  V  V  K  R  G       CD28 and
1141 TATGCCCCACCACGCGACTTCGCAGCCTATCGCTCCCGTTTCTCTGTTGTTAAACGGGGC      4-1BB
                                                                      signaling
401 R  K  K  L  L  Y  I  F  K  Q  P  F  M  R  P  V  Q  T  T  Q       domain
1201 AGAAAGAAGCTCCTGTATATATTCAAACAACCATTTATGAGACCAGTACAAACTACTCAA 421 E  E  D  G  C  S  C  R  F  P  E  E  E  E  G  G  C  E  L  R
1261 GAGGAAGATGGCTGTAGCTGCCGATTTCCAGAAGAAGAAGAAGGAGGATGTGAACTGAGA 441 V  K  F  S  R  S  A  D  A  P  A  Y  Q  Q  G  Q  N  Q  L  Y
1321 GTGAAGTTCAGCAGGAGCGCAGACGCCCCCGCGTACCAGCAGGGCCAGAACCAGCTCTAT 461 N  E  L  N  L  G  R  R  E  E  Y  D  V  L  D  K  R  R  G  R
1381 AACGAGCTCAATCTAGGACGAAGAGAGGAATACGATGTTTTGGACAAGAGACGTGGCCGG 481 D  P  E  M  G  G  K  P  Q  R  R  K  N  P  Q  E  G  L  Y  N       CD3ζ
1441 GACCCTGAGATGGGGGGAAAGCCGCAGAGAAGGAAGAACCCTCAGGAAGGCCTGTACAAT     intra.
                                                                      domain
501 E  L  Q  K  D  K  M  A  E  A  Y  S  E  I  G  M  K  G  E  R
1501 GAACTGCAGAAAGATAAGATGGCGGAGGCCTACAGTGAGATTGGGATGAAAGGCGAGCGC 521 R  R  G  K  G  H  D  G  L  Y  Q  G  L  S  T  A  T  K  D  T
1561 CGGAGGGGCAAGGGGCACGATGGCCTTTACCAGGGTCTCAGTACAGCCACCAAGGACACC 541 Y  D  A  L  H  M  Q  A  L  P  P  R
1621 TACGACGCCCTTCACATGCAGGCCCTGCCCCCTCGC
```

US 11,384,156 B2

ADOPTIVE T-CELL THERAPY USING EMPD-SPECIFIC CHIMERIC ANTIGEN RECEPTORS FOR TREATING IGE-MEDIATED ALLERGIC DISEASES

CROSS-REFERENCE TO RELATED APPLICATION

This application claims the benefit of U.S. Provisional application No. 62/366,328, filed Jul. 25, 2016, the entire disclosure of which is incorporated herein by reference.

SEQUENCE LISTING

The instant application contains a Sequence Listing which has been submitted in ASCII format via EFS-Web and is hereby incorporated by reference in its entirety. Said ASCII copy, created on Jul. 13, 2017 is named 45009-0047-00-US-565303_ST25.txt and is 36,595 bytes in size.

REFERENCE TO GOVERNMENT GRANT

The invention was made with government support under grant no. P20GM10346 and R21AI1119841 awarded by the National Institutes of Health. The government has certain rights in the invention.

FIELD OF THE INVENTION

The invention relates to methods and compositions for the treatment of atopic diseases.

BACKGROUND OF THE INVENTION

An estimated 50 million, or one in five, Americans suffer from allergies. Food allergies cause more than 200 deaths each year, and costs estimated $4,184 annually for each child, or around $25 billion overall (Gupta et al., (2013), *JAMA Pediatr,* 167:1026-1031). In the U.S, asthma affects 25 million people. On an annual basis, asthma directly causes more than 3,300 deaths, indirectly contributes to an additional 7,000 deaths, and costs $56 billion. Approximately 10% of sufferers have severe asthma, which has the highest morbidity and mortality, and consumes over 50% of the health care expenditure attributed to asthma. Severe asthma patients require large doses of corticosteroids in combination with other potentially toxic medications and still may suffer serious symptoms and frequent life-threatening asthma attacks. As a result, severe asthma seriously affects quality of life. According to a 2009 survey of severe asthma conducted by the Asthma and Allergy Foundation of America (AAFA), over a third of patients had made at least 5 emergency department visits and 14% had visited emergency departments twenty times or more. Half of respondents did not consider their current medications effective, two-thirds disliked the cost, and 41% disliked the side-effects. Over half of respondents would prefer to have a "drug-free option" for their asthma (*Severe Asthma Survey.* Asthma and Allergy Foundation of America; 2009). Allergic immune responses trigger the disease in two thirds of patients with asthma and up to 50% of patients with severe asthma ("The ENFUMOSA cross-sectional European multicenter study of the clinical phenotype of chronic severe asthma", European Network for Understanding Mechanisms of Severe Asthma, *Eur Respir J.* 2003; 22(3):470-7).

Allergic reactions are initiated when allergens cross-link specific IgE antibodies bound to the high-affinity receptor FcεRI on mast cells, basophils and eosinophils, thereby triggering degranulation that results in release of inflammatory chemical mediators. IgE therefore plays a central role in allergic asthma and presents an attractive target for therapeutic intervention.

The only drug that targets IgE today is omalizumab (Xolair) for severe allergic asthma. Omalizumab is an IgE-specific humanized monoclonal antibody that depletes IgE. The drug, however, has a relatively short half-life of 1 to 4 weeks (Belliveau et al. (2005), *Med Gen Med* 7:27) an therefore requires repeated administration at high doses (two 150 mg vials every four weeks for most adults), and costs close to $20,000 per year (Kochenderfer et al., (2010), *Blood* 116:4099-4102). A 2007 analysis concluded that omalizumab was not cost-effective for adults with severe asthma (Wu et al., *J Allergy Clin Immunol.* 2007; 120(5):1146-52). Such IgE-specific antibodies do not have an effect on IgE production.

Thus, better approaches for treatment of atopic diseases such as allergic asthma are required. In particular, an approach that persistently suppresses the IgE level over a long period of time with a single treatment would be highly desirable.

SUMMARY OF THE INVENTION

An EMPD-specific chimeric antigen receptor comprises an extracellular ligand binding domain capable of binding EMPD, a transmembrane domain, and an intracellular domain that mediates T cell activation upon binding of EMPD to the extracellular ligand binding domain. In some embodiments, the EMPD-specific chimeric antigen receptor is an isolated EMPD-specific chimeric antigen receptor.

In some embodiments of the EMPD-specific chimeric antigen receptor, the extracellular ligand binding domain comprises a single chain Fv fragment comprising a light chain variable region comprising the complementarity determining regions SEQ ID NO:32, Trp-Ala-Ser and SEQ ID NO:33, and a heavy chain variable region comprising the complementarity determining regions SEQ ID NO:34, SEQ ID NO:35 and SEQ ID NO:36. The light chain variable region and heavy chain variable region may be connected by a sequence of amino acids forming a flexible linker.

In some embodiments of the EMPD-specific chimeric antigen receptor, the extracellular ligand binding domain comprises a single chain Fv fragment comprising a light chain variable region comprising the complementarity determining regions SEQ ID NO:37, Trp-Ala-Ser and SEQ ID NO:38, and a heavy chain variable region comprising the complementarity determining regions SEQ ID NO:39, SEQ ID NO:40 and SEQ ID NO:41. The light chain variable region and heavy chain variable region may be connected by a sequence of amino acids forming a flexible linker.

In some embodiments of the EMPD-specific chimeric antigen receptor, the extracellular ligand binding domain comprises a single chain Fv fragment comprising a light chain variable region comprising the complementarity determining regions SEQ ID NO:42, Leu-Val-Ser and SEQ ID NO:43, and a heavy chain variable region comprising the complementarity determining regions SEQ ID NO:44, SEQ ID NO:45 and SEQ ID NO:46. The light chain variable region and heavy chain variable region may be connected by a sequence of amino acids forming a flexible linker.

In some embodiments of the EMPD-specific chimeric antigen receptor, the extracellular ligand binding domain comprises a single chain Fv fragment comprising a light chain variable region having at least 95% sequence identity with the sequence of amino acids 23 to 136 of SEQ ID NO:7 and a heavy chain variable region having at least 95% sequence identity with the sequence of amino acids 152 to 275 of SEQ ID NO:7. The light chain variable region and heavy chain variable region may be connected by a sequence of amino acids forming a flexible linker.

In some embodiments of the EMPD-specific chimeric antigen receptor, the extracellular ligand binding domain comprises a single chain Fv fragment comprising a light chain variable region having at least 95% sequence identity with the sequence of amino acids 23 to 136 of SEQ ID NO:9 and a heavy chain variable region having at least 95% sequence identity with the sequence of amino acids 152 to 270 of SEQ ID NO:9. The light chain variable region and heavy chain variable region may be connected by a sequence of amino acids forming a flexible linker.

In some embodiments of the EMPD-specific chimeric antigen receptor, the extracellular ligand binding domain comprises a single chain Fv fragment comprising a light chain variable region having at least 95% sequence identity with the sequence of amino acids 23 to 135 of SEQ ID NO:31 and a heavy chain variable region having at least 95% sequence identity with the sequence of amino acids 151 to 268 of SEQ ID NO:31. The light chain variable region and heavy chain variable region may be connected by a sequence of amino acids forming a flexible linker.

In certain embodiments of the aforesaid EMPD-specific chimeric antigen receptors, the recited light chain variable region and/or heavy chain variable region has at least 96%, at least 97%, at least 98%, or at least 99% sequence identity to the indicated corresponding reference amino acid sequence from SEQ ID NO:7, 9 or 31, e.g., a light chain variable region having at least 96%, at least 97%, at least 98% or at least 99% sequence identity to the sequence of amino acids 23 to 135 of SEQ ID NO:31.

In some embodiments of the EMPD-specific chimeric antigen receptor, the extracellular ligand binding domain comprises one of the following single chain Fv fragments:
(i) a single chain Fv fragment comprising a light chain variable region comprising the sequence of amino acids 23 to 136 of SEQ ID NO:7 and a heavy chain variable region comprising the sequence of amino acids 152 to 275 of SEQ ID NO:7, said light chain variable region and heavy chain variable region being connected by a sequence of amino acids forming a flexible linker;
(ii) a single chain Fv fragment comprising a light chain variable region comprising the sequence of amino acids 23 to 136 of SEQ ID NO:9 and a heavy chain variable region comprising the sequence of amino acids 152 to 270 of SEQ ID NO:9, said light chain variable region and heavy chain variable region being connected by a sequence of amino acids forming a flexible linker; or
(iii) a single chain Fv fragment comprising a light chain variable region comprising the sequence of amino acids 23 to 135 of SEQ ID NO:31 and a heavy chain variable region comprising the sequence of amino acids 151 to 268 of SEQ ID NO:31, said light chain variable region and heavy chain variable region being connected by a sequence of amino acids forming a flexible linker.

In certain embodiments, the EMPD-specific chimeric antigen receptor binds to the same EMPD epitope as one of the following single chain Fv fragments:
(i) a single chain Fv fragment comprising a light chain variable region comprising the sequence of amino acids 23 to 136 of SEQ ID NO:7 and a heavy chain variable region comprising the sequence of amino acids 152 to 275 of SEQ ID NO:7;
(ii) a single chain Fv fragment comprising a light chain variable region comprising the sequence of amino acids 23 to 136 of SEQ ID NO:9 and a heavy chain variable region comprising the sequence of amino acids 152 to 270 of SEQ ID NO:9; or
(iii) a single chain Fv fragment comprising a light chain variable region comprising the sequence of amino acids 23 to 135 of SEQ ID NO:31 and a heavy chain variable region comprising the sequence of amino acids 151 to 268 of SEQ ID NO:31.

In certain embodiments, the EMPD-specific chimeric antigen receptor binds to the same EMPD epitope as one of the aforesaid single chain Fv fragments, wherein the light chain variable region and heavy chain variable region of the aforesaid single chain Fv fragments are connected by a sequence of amino acids forming a flexible linker In certain embodiments of the EMPD-specific chimeric antigen receptor, the intracellular domain comprises an intracellular signaling domain comprising at least one immunoreceptor-based activation motif (ITAM).

In certain embodiments of the EMPD-specific chimeric antigen receptor, the intracellular signaling domain comprises a CD3ζ signaling domain. In certain embodiments, the CD3ζ signaling domain comprises the amino acid sequence SEQ ID NO:12. In some embodiments, the CD3ζ signaling domain is encoded by the nucleotide sequence SEQ ID NO: 47.

In certain embodiments, the intracellular domain of the EMPD-specific chimeric antigen receptor comprises a costimulatory signaling domain. In certain embodiments, the costimulatory signaling domain comprises at least the intracellular domain of at least one of 4-1BB, CD27, CD28, CD134 or ICOS. In certain embodiments, the costimulatory signaling domain comprises at least the intracellular domain of CD28 or 4-1BB, or at least the intracellular domain of both CD28 and 4-1BB. In some embodiments, the costimulatory signaling domain comprises the amino acid sequence SEQ ID NO:48. In some embodiments, the costimulatory signaling domain is encoded by the nucleotide sequence SEQ ID NO: 49.

In some embodiments of the EMPD-specific chimeric antigen receptor, the transmembrane domain has the amino acid sequence SEQ ID NO: 22.

In certain embodiments, the EMPD-specific chimeric antigen receptor comprises an amino acid sequence selected from the group of amino sequences consisting of the following:
(a) SEQ ID NO:7;
(b) the sequence of amino acids from amino acid 23 to amino acid 559 of SEQ ID NO:7;
(c) SEQ ID NO:9;
(d) the sequence of amino acids from amino acid 23 to amino acid 554 of SEQ ID NO:9;
(e) SEQ ID NO:31; and
(f) the sequence of amino acids from amino acid 23 to amino acid 552 of SEQ ID NO:31.

In some embodiments, the EMPD-specific chimeric antigen receptor is an isolated chimeric antigen receptor.

An isolated nucleic acid sequence encoding an EMPD-specific chimeric antigen receptor is provided wherein the an EMPD-specific chimeric antigen receptor comprises an extracellular ligand binding domain capable of binding EMPD, a transmembrane domain, and an intracellular domain that mediates T cell activation upon binding of EMPD to the extracellular ligand binding domain.

In some embodiments of the isolated nucleic acid sequence, the encoded extracellular ligand binding domain comprises one of the following single chain Fv fragments:
- (i) a single chain Fv fragment comprising a light chain variable region having at least 95% sequence identity with the sequence of amino acids 23 to 136 of SEQ ID NO:7 and a heavy chain variable region having at least 95% sequence identity with the sequence of amino acids 152 to 275 of SEQ ID NO:7, said light chain variable region and heavy chain variable region being connected by a sequence of amino acids forming a flexible linker;
- (ii) a single chain Fv fragment comprising a light chain variable region having at least 95% sequence identity with the sequence of amino acids 23 to 136 of SEQ ID NO:9 and a heavy chain variable region having at least 95% sequence identity with the sequence of amino acids 152 to 270 of SEQ ID NO:9, said light chain variable region and heavy chain variable region being connected by a sequence of amino acids forming a flexible linker; or
- (iii) a single chain Fv fragment comprising a light chain variable region having at least 95% sequence identity with the sequence of amino acids 23 to 135 of SEQ ID NO:31 and a heavy chain variable region having at least 95% sequence identity with the sequence of amino acids 151 to 268 of SEQ ID NO:31, said light chain variable region and heavy chain variable region being connected by a sequence of amino acids forming a flexible linker.

In certain embodiments of the aforesaid encoded extracellular ligand binding domain, the recited light chain variable region and/or heavy chain variable region has at least 96%, at least 97%, at least 98%, or at least 99% sequence identity to the indicated corresponding reference amino acid sequence from SEQ ID NO:7, 9 or 31, e.g., a light chain variable region having at least 96%, at least 97%, at least 98% or at least 99% sequence identity to the sequence of amino acids 23 to 135 of SEQ ID NO:31.

In some embodiments of the isolated nucleic acid sequence, the encoded extracellular ligand binding domain comprises one of the following single chain Fv fragments:
- (i) a single chain Fv fragment comprising a light chain variable region comprising the sequence of amino acids 23 to 136 of SEQ ID NO:7 and a heavy chain variable region comprising the sequence of amino acids 152 to 275 of SEQ ID NO:7, said light chain variable region and heavy chain variable region being connected by a sequence of amino acids forming a flexible linker;
- (ii) a single chain Fv fragment comprising a light chain variable region comprising the sequence of amino acids 23 to 136 of SEQ ID NO:9 and a heavy chain variable region comprising the sequence of amino acids 152 to 270 of SEQ ID NO:9, said light chain variable region and heavy chain variable region being connected by a sequence of amino acids forming a flexible linker; or
- (iii) a single chain Fv fragment comprising a light chain variable region comprising the sequence of amino acids 23 to 135 of SEQ ID NO:31 and a heavy chain variable region comprising the sequence of amino acids 151 to 268 of SEQ ID NO:31, said light chain variable region and heavy chain variable region being connected by a sequence of amino acids forming a flexible linker.

In some embodiments of the isolated nucleic acid sequence, the encoded EMPD-specific chimeric antigen receptor binds to the same EMPD epitope as one of the following single chain Fv fragments:
- (i) a single chain Fv fragment comprising a light chain variable region comprising the sequence of amino acids 23 to 136 of SEQ ID NO:7 and a heavy chain variable region comprising the sequence of amino acids 152 to 275 of SEQ ID NO:7, said light chain variable region and heavy chain variable region being connected by a sequence of amino acids forming a flexible linker;
- (ii) a single chain Fv fragment comprising a light chain variable region comprising the sequence of amino acids 23 to 136 of SEQ ID NO:9 and a heavy chain variable region comprising the sequence of amino acids 152 to 270 of SEQ ID NO:9, said light chain variable region and heavy chain variable region being connected by a sequence of amino acids forming a flexible linker; or
- (iii) a single chain Fv fragment comprising a light chain variable region comprising the sequence of amino acids 23 to 135 of SEQ ID NO:31 and a heavy chain variable region comprising the sequence of amino acids 151 to 268 of SEQ ID NO:31, said light chain variable region and heavy chain variable region being connected by a sequence of amino acids forming a flexible linker.

In some embodiments of the isolated nucleic acid sequence, the encoded intracellular domain comprises an intracellular signaling domain comprising at least one immunoreceptor-based activation motif (ITAM). In some embodiments of the isolated nucleic acid sequence, the encoded intracellular signaling domain comprises a CD3ζ signaling domain. In some embodiments of the isolated nucleic acid sequence, the encoded CD3ζ signaling domain comprises the amino acid sequence SEQ ID NO: 12. In some embodiments, the CD3ζ signaling domain is encoded by the nucleotide sequence SEQ ID NO: 47.

In some embodiments, the isolated nucleic acid sequence further encodes a costimulatory signaling domain. In some embodiments, the encoded costimulatory signaling domain comprises at least the intracellular domain of at least one of 4-1BB, CD27, CD28, CD134 or ICOS. In some embodiments, the encoded costimulatory signaling domain comprises at least the intracellular domain of CD28 or 4-1BB, or at least the intracellular domain of both CD28 and 4-1BB. In some embodiments, the costimulatory signaling domain comprises the amino acid sequence SEQ ID NO:48. In some embodiments, the costimulatory signaling domain is encoded by the nucleotide sequence SEQ ID NO: 49.

In some embodiments, the isolated nucleic acid sequence encodes an EMPD-specific chimeric antigen receptor having an amino acid sequence selected from the group of amino acid sequences consisting of the following:
- (a) SEQ ID NO:7;
- (b) the sequence of amino acids from amino acid 23 to amino acid 559 of SEQ ID NO:7;
- (c) SEQ ID NO:9;
- (d) the sequence of amino acids from amino acid 23 to amino acid 554 of SEQ ID NO:9;
- (e) SEQ ID NO:31; and
- (f) the sequence of amino acids from amino acid 23 to amino acid 552 of SEQ ID NO:31.

In some embodiments, the isolated nucleic acid sequence comprises a nucleic acid sequence selected from the group consisting of:
- (a) SEQ ID NO:6;
- (b) the sequence of nucleotides from nucleotide 67 to nucleotide 1677 of SEQ ID NO:6;
- (c) SEQ ID NO:8;
- (d) the sequence of nucleotides from nucleotide 67 to nucleotide 1662 of SEQ ID NO:8;
- (e) SEQ ID NO:30; and (f) the sequence of nucleotides from nucleotide 67 to nucleotide 1656 of SEQ ID NO: 30.

According to other embodiments, a T cell is provided comprising a nucleic acid sequence encoding an EMPD-specific chimeric antigen receptor, wherein the EMPD-specific chimeric antigen receptor comprises an extracellular ligand binding domain capable of binding EMPD, a transmembrane domain, and an intracellular domain that mediates T cell activation upon binding of EMPD to the extracellular ligand binding domain.

According to other embodiments, a T cell expressing an EMPD-specific chimeric antigen receptor is provided, wherein the EMPD-specific chimeric antigen receptor comprises an extracellular ligand binding domain capable of binding EMPD, a transmembrane domain, and an intracellular domain that mediates T cell activation upon binding of EMPD to the extracellular ligand binding domain.

In some embodiments of the T cell, the extracellular ligand binding domain of the EMPD-specific chimeric antigen receptor expressed by the T cell comprises a single chain Fv fragment comprising a light chain variable region comprising the complementarity determining regions SEQ ID NO:32, Trp-Ala-Ser and SEQ ID NO:33, and a heavy chain variable region comprising the complementarity determining regions SEQ ID NO:34, SEQ ID NO:35 and SEQ ID NO:36. The light chain variable region and heavy chain variable region may be connected by a sequence of amino acids forming a flexible linker.

In some embodiments of the T cell, the extracellular ligand binding domain of the EMPD-specific chimeric antigen receptor expressed by the T cell comprises a single chain Fv fragment comprising a light chain variable region comprising the complementarity determining regions SEQ ID NO:37, Trp-Ala-Ser and SEQ ID NO:38, and a heavy chain variable region comprising the complementarity determining regions SEQ ID NO:39, SEQ ID NO:40 and SEQ ID NO:41. The light chain variable region and variable heavy chain variable region may be connected by a sequence of amino acids forming a flexible linker.

In some embodiments of the T cell, the extracellular ligand binding domain of the EMPD-specific chimeric antigen receptor expressed by the T cell comprises a single chain Fv fragment comprising a light chain variable region comprising the complementarity determining regions SEQ ID NO:42, Leu-Val-Ser and SEQ ID NO:43, and a heavy chain variable region comprising the complementarity determining regions SEQ ID NO:44, SEQ ID NO:45 and SEQ ID NO:46. The light chain variable region and variable heavy chain variable region may be connected by a sequence of amino acids forming a flexible linker.

In some embodiments of the T cell, the extracellular ligand binding domain of the EMPD-specific chimeric antigen receptor expressed by the T cell comprises a single chain Fv fragment comprising a light chain variable region having at least 95% sequence identity with the sequence of amino acids 23 to 136 of SEQ ID NO:7 and a heavy chain variable region having at least 95% sequence identity with the sequence of amino acids 152 to 275 of SEQ ID NO:7, said light chain variable region and heavy chain variable region being connected by a sequence of amino acids forming a flexible linker.

In some embodiments of the T cell, the extracellular ligand binding domain of the EMPD-specific chimeric antigen receptor expressed by the T cell comprises a single chain Fv fragment comprising a light chain variable region having at least 95% sequence identity with the sequence of amino acids 23 to 136 of SEQ ID NO:9 and a heavy chain variable region having at least 95% sequence identity with the sequence of amino acids 152 to 270 of SEQ ID NO:9, said light chain variable region and heavy chain variable region being connected by a sequence of amino acids forming a flexible linker.

In some embodiments of the T cell, the extracellular ligand binding domain of the EMPD-specific chimeric antigen receptor expressed by the T cell comprises a single chain Fv fragment comprising a light chain variable region having at least 95% sequence identity with the sequence of amino acids 23 to 135 of SEQ ID NO:31 and a heavy chain variable region having at least 95% sequence identity with the sequence of amino acids 151 to 268 of SEQ ID NO:31, said light chain variable region and heavy chain variable region being connected by a sequence of amino acids forming a flexible linker.

In certain embodiments of the aforesaid T cells, the recited light chain variable region and/or heavy chain variable region has at least 96%, at least 97%, at least 98%, or at least 99% sequence identity to the indicated corresponding reference amino acid sequence from SEQ ID NO:7, 9 or 31, e.g., a light chain variable region having at least 96%, at least 97%, at least 98% or at least 99% sequence identity to the sequence of amino acids 23 to 135 of SEQ ID NO:31.

In some embodiments of the T cell, the extracellular ligand binding domain of the EMPD-specific chimeric antigen receptor expressed by the T cell comprises one of the following single chain Fv fragments:
  (i) a single chain Fv fragment comprising a light chain variable region comprising the sequence of amino acids 23 to 136 of SEQ ID NO:7 and a heavy chain variable region comprising the sequence of amino acids 152 to 275 of SEQ ID NO:7, said light chain variable region and heavy chain variable region being connected by a sequence of amino acids forming a flexible linker;
  (ii) a single chain Fv fragment comprising a light chain variable region comprising the sequence of amino acids 23 to 136 of SEQ ID NO:9 and a heavy chain variable region comprising the sequence of amino acids 152 to 270 of SEQ ID NO:9, said light chain variable region and heavy chain variable region being connected by a sequence of amino acids forming a flexible linker; or
  (iii) a single chain Fv fragment comprising a light chain variable region comprising the sequence of amino acids 23 to 135 of SEQ ID NO:31 and a heavy chain variable region comprising the sequence of amino acids 151 to 268 of SEQ ID NO:31, said light chain variable region and heavy chain variable region being connected by a sequence of amino acids forming a flexible linker.

In some embodiments of the T cell, the EMPD-specific chimeric antigen receptor expressed by the T cell binds to the same EMPD epitope as one of the following single chain Fv fragments:
  (i) a single chain Fv fragment comprising a light chain variable region comprising the sequence of amino acids 23 to 136 of SEQ ID NO:7 and a heavy chain variable region comprising the sequence of amino acids 152 to 275 of SEQ ID NO:7, said light chain variable region and heavy chain variable region being connected by a sequence of amino acids forming a flexible linker;
  (ii) a single chain Fv fragment comprising a light chain variable region comprising the sequence of amino acids 23 to 136 of SEQ ID NO:9 and a heavy chain variable region comprising the sequence of amino acids 152 to 270 of SEQ ID NO:9, said light chain variable region and heavy chain variable region being connected by a sequence of amino acids forming a flexible linker; or (iii) a single chain Fv fragment comprising a light chain variable region comprising the sequence of amino acids 23 to 135 of SEQ ID NO:31 and a heavy chain variable region comprising the sequence of amino acids 151 to 268 of SEQ ID NO:31, said light chain variable region and heavy chain variable region being connected by a sequence of amino acids forming a flexible linker.

In certain embodiments of the T cell, the intracellular domain of the EMPD-specific chimeric antigen receptor expressed on the T cell comprises an intracellular signaling domain comprising at least one immunoreceptor-based activation motif (ITAM).

In certain embodiments, the intracellular signaling domain comprises a CD3ζ signaling domain. In certain embodiments, the CD3ζ signaling domain comprises the amino acid sequence SEQ ID NO: 12. In some embodiments, the CD3ζ signaling domain is encoded by the nucleotide sequence SEQ ID NO: 47.

In certain embodiments of the T cell, the EMPD-specific chimeric antigen receptor expressed on the T cell comprises a costimulatory signaling domain. In certain embodiments, the costimulatory signaling domain comprises at least the intracellular domain of at least one of 4-1BB, CD27, CD28, CD134 or ICOS. In certain embodiments, the costimulatory signaling domain comprises at least the intracellular domain of CD28 or 4-1BB, or at least the intracellular domains of both CD28 and 4-1BB. In some embodiments, the costimulatory signaling domain comprises the amino acid sequence SEQ ID NO:48. In some embodiments, the costimulatory signaling domain is encoded by the nucleotide sequence SEQ ID NO: 49.

In certain embodiments of the T cell, the transmembrane domain of the EMPD-specific chimeric antigen receptor expressed by the T cell has the amino acid sequence SEQ ID NO: 22.

In certain embodiments of the T cell, the EMPD-specific chimeric antigen receptor expressed by the T cell comprises an amino acid sequence selected from the group of amino acid sequences consisting of the following:
  (a) SEQ ID NO:7;
  (b) the sequence of amino acids from amino acid 23 to amino acid 559 of SEQ ID NO:7;
  (c) SEQ ID NO:9;
  (d) the sequence of amino acids from amino acid 23 to amino acid 554 of SEQ ID NO:9;
  (e) SEQ ID NO:31; and
  (f) the sequence of amino acids from amino acid 23 to amino acid 552 of SEQ ID NO:31.

According to other embodiments, a vector is provided comprising a nucleic acid sequence encoding an EMPD-specific chimeric antigen receptor wherein the an EMPD-specific chimeric antigen receptor comprises an extracellular ligand binding domain capable of binding EMPD, a transmembrane domain, and an intracellular domain that mediates T cell activation upon binding of EMPD to the extracellular ligand binding domain.

In some embodiments of the vector, the encoded extracellular ligand binding domain comprises one of the following single chain Fv fragments:
  (i) a single chain Fv fragment comprising a light chain variable region having at least 95% sequence identity with the sequence of amino acids 23 to 136 of SEQ ID NO:7 and a heavy chain variable region having at least 95% sequence identity with the sequence of amino acids 152 to 275 of SEQ ID NO:7, said light chain variable region and heavy chain variable region being connected by a sequence of amino acids forming a flexible linker;
  (ii) a single chain Fv fragment comprising a light chain variable region having at least 95% sequence identity with the sequence of amino acids 23 to 136 of SEQ ID NO:9 and a heavy chain variable region having at least 95% sequence identity with the sequence of amino acids 152 to 270 of SEQ ID NO:9, said light chain variable region and heavy chain variable region being connected by a sequence of amino acids forming a flexible linker; or
  (iii) a single chain Fv fragment comprising a light chain variable region having at least 95% sequence identity with the sequence of amino acids 23 to 135 of SEQ ID NO:31 and a heavy chain variable region having at least 95% sequence identity with the sequence of amino acids 151 to 268 of SEQ ID NO:31, said light chain variable region and heavy chain variable region being connected by a sequence of amino acids forming a flexible linker.

In certain embodiments of the aforesaid encoded extracellular ligand binding domain, the recited light chain variable region and/or heavy chain variable region has at least 96%, at least 97%, at least 98%, or at least 99% sequence identity to the indicated corresponding reference amino acid sequence from SEQ ID NO:7, 9 or 31, e.g., a light chain variable region having at least 96%, at least 97%, at least 98% or at least 99% sequence identity to the sequence of amino acids 23 to 135 of SEQ ID NO:31.

In some embodiments of the vector, the encoded extracellular ligand binding domain comprises one of the following single chain Fv fragments:
  (i) a single chain Fv fragment comprising a light chain variable region comprising the sequence of amino acids 23 to 136 of SEQ ID NO:7 and a heavy chain variable region comprising the sequence of amino acids 152 to 275 of SEQ ID NO:7, said light chain variable region and heavy chain variable region being connected by a sequence of amino acids forming a flexible linker;
  (ii) a single chain Fv fragment comprising a light chain variable region comprising the sequence of amino acids 23 to 136 of SEQ ID NO:9 and a heavy chain variable region comprising the sequence of amino acids 152 to 270 of SEQ ID NO:9, said light chain variable region and heavy chain variable region being connected by a sequence of amino acids forming a flexible linker; or
  (iii) a single chain Fv fragment comprising a light chain variable region comprising the sequence of amino acids 23 to 135 of SEQ ID NO:31 and a heavy chain variable region comprising the sequence of amino acids 151 to 268 of SEQ ID NO:31, said light chain variable region and heavy chain variable region being connected by a sequence of amino acids forming a flexible linker.

In some embodiments of the vector, the encoded EMPD-specific chimeric antigen receptor binds to the same EMPD epitope as one of the following single chain Fv fragments:
  (i) a single chain Fv fragment comprising a light chain variable region comprising the sequence of amino acids 23 to 136 of SEQ ID NO:7 and a heavy chain variable region comprising the sequence of amino acids 152 to 275 of SEQ ID NO:7, said light chain variable region and heavy chain variable region being connected by a sequence of amino acids forming a flexible linker;
  (ii) a single chain Fv fragment comprising a light chain variable region comprising the sequence of amino acids 23 to 136 of SEQ ID NO:9 and a heavy chain variable region comprising the sequence of amino acids 152 to 270 of SEQ ID NO:9, said light chain variable region and heavy chain variable region being connected by a sequence of amino acids forming a flexible linker; or (iii) a single chain Fv fragment comprising a light chain variable region comprising the sequence of amino acids 23 to 135 of SEQ ID NO:31 and a heavy chain variable region comprising the sequence of amino acids 151 to 268 of SEQ ID NO:31, said light chain variable region and heavy chain variable region being connected by a sequence of amino acids forming a flexible linker.

In some embodiments of the vector, the encoded intracellular signaling domain comprises at least one immunoreceptor-based activation motif (ITAM). In some embodiments of the vector, the encoded intracellular signaling domain comprises a CD3 ζ signaling domain. In some embodiments of the vector, the encoded CD3ζ signaling domain has the amino acid sequence SEQ ID NO: 12. In some embodiments, the CD3ζ signaling domain is encoded by the nucleotide sequence SEQ ID NO: 47.

In some embodiments of the vector, the encoded intracellular domain comprises a costimulatory signaling domain. In some embodiments, the encoded costimulatory signaling domain comprises at least the intracellular domain of at least one of 4-1BB, CD27, CD28, CD134 or ICOS. In some embodiments, the encoded costimulatory signaling domain comprises at least the intracellular domain of CD28 or 4-1BB, or at least the intracellular domains of both CD28 and 4-1BB. In some embodiments, the encoded costimulatory signaling domain comprises the amino acid sequence SEQ ID NO:48. In some embodiments, the costimulatory domain is encoded by the nucleotide sequence SEQ ID NO: 49.

In some embodiments, the vector encodes an EMPD-specific chimeric antigen receptor having an amino acid sequence selected from the group of amino sequences consisting of the following:

(a) SEQ ID NO:7;
(b) the sequence of amino acids from amino acid 23 to amino acid 559 of SEQ ID NO:7;
(c) SEQ ID NO:9;
(d) the sequence of amino acids from amino acid 23 to amino acid 554 of SEQ ID NO:9;
(e) SEQ ID NO:31; and
(f) the sequence of amino acids from amino acid 23 to amino acid 552 of SEQ ID NO:31.

In some embodiments, the vector comprises a nucleic acid sequence selected from the group consisting of:

(a) SEQ ID NO:6;
(b) the sequence of nucleotides from nucleotide 67 to nucleotide 1677 of SEQ ID NO:6;
(c) SEQ ID NO:8;
(d) the sequence of nucleotides from nucleotide 67 to nucleotide 1662 of SEQ ID NO:8;
(e) SEQ ID NO:30; and
(f) the sequence of nucleotides from nucleotide 67 to nucleotide 1656 of SEQ ID NO: 30.

According to other embodiments, a method for stimulating a T cell-mediated immune response to cells expressing mIgE in a subject is provided. The method comprises administering to the subject an effective amount of a T cells, according to any of the aforesaid T cell embodiments. In certain embodiments, the T cells comprise autologous T cells that are removed from the subject and engineered ex vivo to express the aforesaid chimeric antigen receptor (CAR) and administered to the subject.

According to other embodiments, a method for treating an IgE-mediated allergic disease in a subject in need of such treatment is provided. The method comprises administering to the subject an effective amount of T cells, according to any of the aforesaid T cell embodiments. According to another embodiment, a method of preventing an IgE-mediated allergic disease in a subject at risk of such disease is also provided. In certain embodiments of the aforesaid treatment and prevention methods, the T cells comprise autologous T cells that are removed from the subject and engineered ex vivo to express the aforesaid EMPD-specific chimeric antigen receptor and administered to the subject. In certain embodiments, the disease is selected from the group consisting of allergic asthma, food allergy, atopic dermatitis, allergic rhinitis, allergic rhinoconjunctivitis, chronic urticaria and systematic anaphylaxis.

Also provided are the aforesaid T cells for use in stimulating a T cell-mediated immune response to cells expressing mIgE in a subject. Also provided are the aforesaid T cells for treating an IgE-mediated allergic disease in a subject in need of such treatment, or for preventing an IgE-mediated allergic disease in a subject at risk of such disease. Also provided is a medicament or a pharmaceutical composition for use in stimulating a T cell-mediated immune response to cells expressing mIgE in a subject. Also provided is a medicament or a pharmaceutical composition for use in treating an IgE-mediated allergic disease, or for preventing an IgE-mediated allergic disease in a subject at risk of such disease.

As envisioned in the present invention with respect to the disclosed compositions of matter and methods, in one aspect the embodiments of the invention comprise the components and/or steps disclosed herein. In another aspect, the embodiments of the invention consist essentially of the components and/or steps disclosed herein. In yet another aspect, the embodiments of the invention consist of the components and/or steps disclosed herein.

DESCRIPTION OF THE FIGURES

FIGS. 3a and 3b, combined, are a representation of the nucleotide (SEQ ID NO:6) and amino acid (SEQ ID NO:7) sequences of an EMPD-specific CAR based on an scFv designated 1D2F11. The positions of the various CAR elements in the amino acid sequence are: Ig kappa signal peptide (1-22); scFv $V_L$ (23-136); scFv linker (137-151); scFv $V_H$ (152-275); CD8 hinge, transmembrane domain and intracellular domain (276-358); CD28 and 4-1BB signaling domains (359-447); and CD3ζ intracellular domain (448-559).

FIGS. 5a and 5b, combined, are a representation of the nucleotide (SEQ ID NO:8) and amino acid (SEQ ID NO:9) sequences of the EMPD-specific CAR based on scFv 2E3E10. The positions of the various CAR elements in the amino acid sequence are: Ig kappa signal peptide (1-22); scFv $V_L$ (23-136); scFv linker (137-151); scFv $V_H$ (152-270); CD8 hinge, transmembrane domain and intracellular domain (271-353); CD28 and 4-1BB signaling domains (354-442); and CD3ζ intracellular domain (443-554).

FIGS. 6a and 6b, combined, are a representation of the nucleotide (SEQ ID NO:30) and amino acid (SEQ ID NO:31) sequences of an EMPD-specific CAR based on an scFv designated 1C8G8. The positions of the various CAR elements in the amino acid sequence are: Ig kappa signal peptide (1-22); scFv $V_L$ (23-135); scFv linker (136-150); scFv $V_H$ (151-268); CD28 hinge, transmembrane domain and intracellular domain (269-351); CD28 and 4-1BB signaling domains (352-440); and CD3ζ intracellular domain (441-552).

DEFINITIONS

Figure 1:
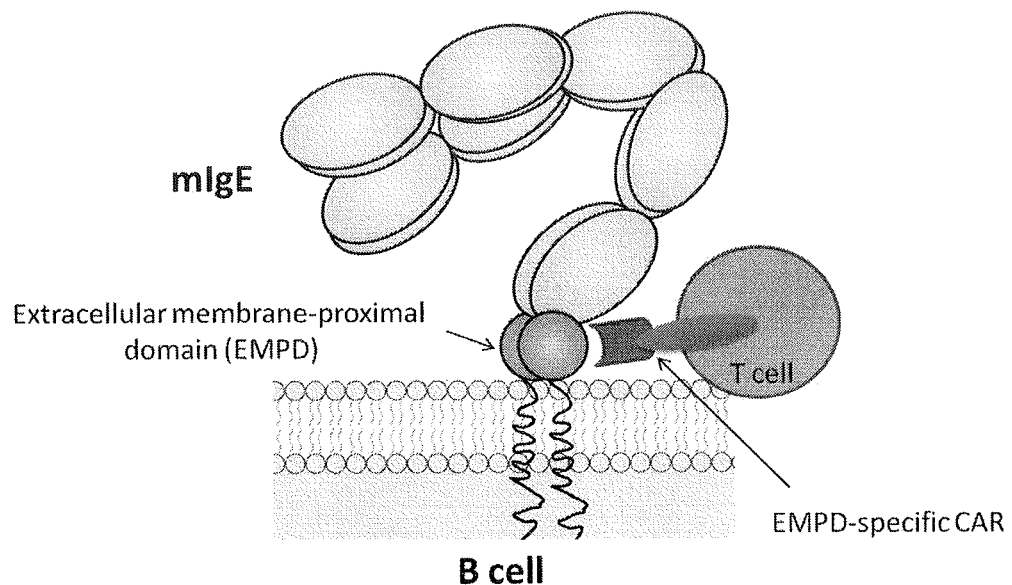
FIG. 1 is an illustration of the action of an EMPD-specific CAR according to the present invention in redirecting T cell response specifically to cells expressing mIgE. The EMPD-specific CAR is shown binding to the EMPD of mIgE on an a B cell expressing mIgE. The binding triggers TCR signaling, T cell activation and target cell killing.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element. Thus, recitation of "a cell", for example, includes a plurality of the cells of the same type.

"About" as used herein when referring to a measurable value such as an amount, a temporal duration, and the like, is meant to encompass variations of +/−20% or +/−10%, more preferably +/−5%, even more preferably +/−1%, and still more preferably +/−0.1% from the specified value, as such variations are appropriate to perform the disclosed methods.

As used herein, the term "autologous" is meant to refer to any material derived from the same individual to which it is later to be re-introduced into the individual.

Unless otherwise specified herein, the terms "antibody" and "antibodies" broadly encompass naturally-occurring forms of antibodies (e.g., IgG, IgA, IgM, IgE) and recombinant antibodies as well as derivatives have at least an antigenic binding site. Antibody derivatives may comprise a protein or chemical moiety conjugated to an antibody.

A "humanized antibody" refers to an antibody in which the complementarity defining regions (CDRs) of an antibody of a non-human mammal, e.g., mouse, are grafted to a human antibody. The variable domain of each of an antibody heavy chain and light chain comprise three CDRs; the intervening sequence segments are "framework segments". Each variable domain is composed of four framework segments. In a humanized antibody, the framework segments are typically of human origin.

A "single chain antibody", also known as a "single-chain variable fragment" (scFv) is a fusion protein of the variable regions of the heavy and light chains of an immunoglobulin, wherein the regions are optionally connected by a linker. As used herein, "single chain antibody" or "single-chain variable fragment" includes such fusion proteins, and also multimers (linear or branched) formed of such fusion proteins.

An "effective amount" as used herein, means an amount which provides a therapeutic or prophylactic benefit.

By "EMPD" is meant the extracellular membrane binding domain of a membrane IgE (mIgE), which is not found on serum IgE, or any other Ig isotype. "EMPD" includes allelic variations thereof. In human mIgE, the EMPD consists of a 52 amino acid segment.

By "EMPD-specific chimeric antigen receptor is meant a chimeric antigen receptor having an extracellular ligand-binding domain which recognizes and binds with EMPD, but does not substantially recognize or bind other molecules.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

The term "extracellular ligand-binding domain" as used herein is defined as an oligo- or polypeptide that is capable of binding a ligand.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

As used herein, the term "fusion protein" or "fusion polypeptide" is a polypeptide comprised of at least two polypeptides and optionally a linking sequence, and that are operatively linked into one continuous protein. The two polypeptides linked in a fusion protein are typically derived from two independent sources (i.e., not from the same parental polypeptide), and therefore a fusion protein comprises two linked polypeptides not normally found linked in nature. Typically, the two polypeptides can be operably attached directly by a peptide bond, or may be connected by a linking group, such as a spacer domain. An example of a fusion polypeptide is a polypeptide that functions as a receptor for an antigen, wherein an antigen binding polypeptide forming an extracellular domain is fused to a different polypeptide, forming a "chimeric antigen receptor".

The term "signaling domain" refers to the functional portion of a protein which acts by transmitting information within the cell to regulate cellular activity via defined signaling pathways by generating second messengers or functioning as effectors by responding to such messengers. An "intracellular signaling domain" refers to the intracellular portion of a signaling domain.

By "IgE-mediated allergic disease" is meant an allergic disease caused, at least in part, by an IgE-mediated hypersensitivity reaction. Examples of such diseases include asthma, food allergy, atopic dermatitis, allergic rhinitis, allergic rhinoconjunctivitis, chronic urticaria and systematic anaphylaxis.

By "mutant" with respect to a polypeptide or portion thereof (such as a functional domain of a polypeptide) is meant a polypeptide that differs in amino acid sequence from the corresponding wild type polypeptide amino acid sequence by deletion, substitution or insertion of at least one amino acid. A "deletion" in an amino acid sequence or polypeptide is defined as a change in amino acid sequence in which one or more amino acid residues are absent as compared to the wild-type protein. As used herein an "insertion" or "addition" in an amino acid sequence or polypeptide is a change in an amino acid sequence that has resulted in the addition of one or more amino acid residues as compared to the wild-type protein. Preferably, the mutation comprises the substitution of one or more amino acids, preferably the substitution of 1, 2 or 3 amino acids. A greater number of substitutions are possible.

As used herein "substitution" in an amino acid sequence or polypeptide results from the replacement of one or more amino acids by different amino acids, respectively, as compared to the wild-type polypeptide.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

An "isolated nucleic acid" refers to a nucleic acid segment or fragment which has been separated from sequences which flank it in a naturally occurring state, i.e., a DNA fragment which has been removed from the sequences which are normally adjacent to the fragment, i.e., the sequences adjacent to the fragment in a genome in which it naturally occurs. The term also applies to nucleic acids which have been substantially purified from other components which naturally accompany the nucleic acid, i.e., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used, "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

The term "linker", also referred to as a "spacer" or "spacer domain" as used herein, refers to a an amino acid or sequence of amino acids that that is optionally located between two amino acid sequences in a fusion protein of the invention.

The term "hinge" or "hinge region" refers to a flexible polypeptide connector region providing structural flexibility and spacing to flanking polypeptide regions. The hinge can consist of natural or synthetic polypeptides.

The term "operably linked" (and also the term "under transcriptional control") refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"Parenteral" administration of an immunogenic composition includes, e.g., subcutaneous (s.c.), intravenous (i.v.), intramuscular (i.m.), or intrasternal injection, or infusion techniques.

The terms "patient," "subject," "individual," and the like are used interchangeably herein, and refer to a human being.

The term "polynucleotide" is a chain of nucleotides, also known as a "nucleic acid". As used herein polynucleotides include, but are not limited to, all nucleic acid sequences which are obtained by any means available in the art, and include both naturally occurring and synthetic nucleic acids.

The terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" means a DNA sequence recognized by the synthetic machinery of the cell, or introduced synthetic machinery, required to initiate the specific transcription of a polynucleotide sequence.

The term "transfected" or "transformed" or "transduced" means to a process by which exogenous nucleic acid is transferred or introduced into the host cell. A "transfected" or "transformed" or "transduced" cell is one which has been transfected, transformed or transduced with exogenous nucleic acid. The transfected/transformed/transduced cell includes the primary subject cell and its progeny.

To "treat" a disease as the term is used herein, means to reduce the frequency or severity of at least one sign or symptom of a disease or disorder experienced by a subject.

A "vector" is a composition of matter which comprises an isolated nucleic acid and which can be used to deliver the isolated nucleic acid to the interior of a cell. Examples of vectors include but are not limited to, linear polynucleotides, polynucleotides associated with ionic or amphiphilic compounds, plasmids, and viruses. Thus, the term "vector" includes an autonomously replicating plasmid or a virus. The term is also construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Where any amino acid sequence is specifically referred to by a Swiss Prot. or GENBANK Accession number, the sequence is incorporated herein by reference. Information associated with the accession number, such as identification of signal peptide, extracellular domain, transmembrane domain, promoter sequence and translation start, is also incorporated herein in its entirety by reference.

DETAILED DESCRIPTION OF THE INVENTION

IgE is the key mediator of allergic diseases. In particular, IgE, and specifically the interaction of IgE with FcεRI, is central to the pathogenesis of allergy and asthma.

IgE is found in two forms, a secreted serum immunoglobulin form and a membrane-bound IgE (mIgE), which comprise distinct mRNA splice variants. Membrane IgE contains an additional extracellular 52-amino acid sequence that has been called the extracellular membrane-proximal domain (EMPD), M1, me.1, or CεmX. EMPD is not found on serum IgE, or any other Ig isotype. The gene segment encoding EMPD is only found in the membrane-bound immunoglobulin ε chain (mc) of recently evolved primates, namely, the New-world monkeys and Old-world monkeys (including Homo sapiens) (Wu et al., *Immunogenetics* 64, 279-287 (2012)). EMPD is located between the CH4 domain and the C-terminal membrane-anchoring segment of mc. For a schematic of the position of EMPD in ME see FIG. 1*a* of Chu et al., *Nat Commun.* 5:3139 IDOI:10.1038/ncomms41391<nature.com/naturecommunications. As of 2014, only two allelic forms differing by a leucine or valine at position 16 along the EMPD sequence (which generally does not affect antigenicity) have been found (Wan et al., *Immunogenetics* 62, 273-280 (2010); Chu et al., supra).

The amino acid sequence of the $^{16}$leucine EMPD form is, from N- to C-terminus: GLAGGSAQSQRAP-DRLLCHSGQQQGLPRAAGGSVPH-PRCHCGAGRADWPGPP (SEQ ID NO:1). The amino acid sequence of the $^{16}$valine EMPD form is, from N- to C-terminus: GLAGGSAQSQRAPDRVLCHSGQQQGL-PRAAGGSVPHPRCHCGAGRADWPGPP (SEQ ID NO:2). Two cysteines in EMPD form an intrachain disulfide bond (Cys-18 with Cys-39 or Cys-41), while the other cysteine forms an interchain bridge (Bestagno et al., *Biochemistry* 40, 10686-10692 (2001)).

According to the present invention, IgE-expressing B cells, the source of IgE, are targeted using adoptive T cell therapy (ACT) to achieve long-term suppression of IgE production. Autologous T cells are engineered to stably express chimeric antigen receptors (CARs) that are specific for IgE-expressing B cells ex vivo. The EMPD-based CAR design takes advantage of the specific binding between a contained EMPD-specific antigen-binding domain on the CAR, located in the CAR ectodomain, that directs T cell specificity to cells expressing mIgE. The EMPD-targeting extracellular domain of the CAR binds the target molecule mIgE. The ligand-binding extracellular domain may be, for example, an scFv-derived from a monoclonal antibody which specifically binds to a determinant in EMPD. The CAR further comprises a transmembrane domain and an intracellular domain that mediates T cell activation upon EMPD binding to the ligand-binding extracellular domain. The intracellular domain comprises a primary signaling domain and/or one or more co-stimulatory signaling domains. T cell activation is achieved through the primary signaling domain contained in the intracellular domain of the CAR, or contained in the intracellular domain of other molecules that are associated with the CAR. The CAR may optionally and preferably comprise one or more co-stimulatory signaling domains contained in the intracellular domain of the CAR, or contained in the intracellular domain of other molecules that are associated with the CAR. In certain embodiments, a primary signaling domain comprises at least one immunoreceptor tyrosine-based activation motif ("ITAM"). The primary intracellular signaling domain and co-stimulatory signaling domain(s) function for signaling and T-cell activation. In one embodiment, the intracellular signaling domain comprises the intracellular signaling domain derived from CD3ζ, for signaling and T-cell activation.

The activating signal provided by the CAR is able to endow the CAR⁺ T-cells with the ability to lyse target cells and secret cytokines in response to antigen binding.

In one embodiment, a patient's T cells are isolated, expanded, and genetically modified to express EMPD-based chimeric antigen receptors (CARs), which enable T cell recognition of cells expressing the transmembrane form of IgE (mIgE), which is present on all IgE-producing B cells. The modified T cells are then transferred back to the patient to seek and destroy IgE-producing B cells, and thus source of IgE. The transferred cells develop a memory phenotype and continuously destroy newly emerged IgE-expressing cells. Previous studies using other types of T-cell therapy have shown that transferred T cells exhibit memory phenotype and persist for more than 10 years. For example, ACT using CD19-specific CARs led to complete remission in patients with B cell leukemia and lymphoma. See, e.g., Brentjens et al., (2013) Sci Transl Med 5:177ra138. Importantly, genetically modified T cells have been shown to persist for more than a decade in patients without adverse effects (Scholler et al., (2012) Sci Transl Med 4:132ra153), demonstrating the long term effectiveness and safety of ACT. It was estimated that a single CAR⁺ T cell is capable of killing more than 1000 target cells (Id.).

Thus, the present CAR-based adoptive T-cell therapy (ACT) approach for targeting IgE-expressing B cells is believed to be capable of providing long-term control or remission of IgE-mediated allergic diseases that may not be easily managed with currently available medications. Control of disease is achieved without the need for frequent administration, a disadvantage that limits to the range of applications of IgE monoclonal antibody therapy. Targeting the source of IgE, the IgE-expressing B cells, therefore, provides an attractive alternative to administration of IgE monoclonal antibodies.

The present CAR-based adoptive T-cell therapy (ACT) approach overcomes the limitations of monoclonal antibody based treatments, such as treatment with omalizumab, by eliminating the source of IgE production. IgE is produced by B cells that are class-switched with help from Th2 cells. IgE-expressing B cells go through different developmental stages that include germinal center B cells, plasmablasts, plasma cells, and memory B cells (Talay et al., (2012) Nat Immunol 13:396-404). These cells uniquely express mIgE on the cell surface that can be used as a molecular target. According to the present invention, T cells (preferably autologous T cells) are engineered to express a CAR that recognizes cells expressing mIgE. The engineering redirects T cell specificity to the mIgE-expressing cells, to destroy those cells.

The CAR is designed to work in the presence of free IgE because, due to its specificity for mIgE, it is not blocked by free IgE. The CAR based on ligand binding to EMPD thus specifically directs T cell killing to cells expressing mIgE.

Extracellular Ligand-Binding Domain

The CAR comprises an extracellular ligand-binding domain that specifically binds EMPD. In certain embodiments, the ligand-binding domain comprises functional features of properties of an antibody. The ligand-binding domain can be any domain that binds to an antigen present on EMPD, including but not limited to antigen recognition domains derived from any one or more of monoclonal antibodies, polyclonal antibodies, synthetic antibodies, human antibodies, humanized antibodies, and fragments thereof. In some instances, it is beneficial for the ligand binding domain to be derived from the same species in which the EMPD-specific CAR will ultimately be used in. For example, for use in humans, it may be beneficial for the ligand-binding domain of the CAR to comprise a human antibody or a fragment thereof. Thus, in one embodiment, the antigen biding domain portion comprises a human antibody or a fragment thereof.

In preferred embodiments, the ligand-binding domain is derived from the antigen-binding portion of a monoclonal antibody specific for EMPD, such as an scFv derived from such a monoclonal antibody. In another embodiment, the ligand-binding domain is derived from other forms including, for example, Fv, Fab, and (Fab')₂, as well as bi-functional (i.e. bi-specific) hybrid antibodies (e.g., Lanzavecchia et al., Eur. J. Immunol. 17, 105 (1987)).

In a preferred embodiment, the extracellular ligand-binding domain comprises a single chain variable fragment (scFv) comprising the light ($V_L$) and the heavy ($V_H$) variable regions of an EMPD-specific monoclonal antibody joined by a flexible linker. The linker is a peptide linker, i.e., the linker is composed of amino acid residues. The residues for the linker may be selected from naturally occurring amino acids, non-naturally occurring amino acids, and modified amino acids. The linker will typically connect the carboxy terminus of the heavy chain variable region to the amino terminus of said light chain variable region. The reverse is also possible, i.e., using the linker to connect the carboxy terminus of the light chain variable region to the amino terminus of the heavy chain variable region. The linker may comprise any number of amino acids. The linker may thus comprise, for example, 1, 2, 3, 4, 5, 6, 7, 8, 9, 10, 11, 12, 13, 14, 15, 16, 17, 18, 19, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, or more amino acids. In some embodiments, the linker may be composed of from 3 to 60 amino acid residues, from 3 to 40 amino acids, from 3 to 30 amino acids, from 3 to 24 amino acids, from 3 to 18 amino acids, or from 3 to 15 amino acids. In one embodiment, the linker comprises the amino acid sequence Gly-Ser, or contains repeats thereof. See, e.g., Huston, et al., Methods in Enzymology, 203:46-88 (1991).

Hybridoma clones that secrete mAbs specific for EMPD are produced as a source of EMPD-specific scFvs. Hybridomas generating such monoclonal antibodies may be prepared by standard hybridoma technology. The immunogen used for immunization of appropriate animal hosts for EMPD-immune splenocytes for anti-EMPD hybridoma preparation can comprise any immunogen capable of generating EMPD-specific antibodies. For example, the immunogen may comprise all or part of the EMPD, particularly an immunogenic fragment of EMPD. EMPD-specific hybridomas producing antibody of the requisite antigen-binding specificity and avidity are screened by conventional screening techniques. For example, mAb specificity can be tested by screening for binding of synthesized EMPD peptides or cell lines expressing mIgE. The variable regions of the hybridoma DNA sequences encoding the mAb heavy and light chains are then cloned and formed into an appropriate scFv-encoding construct.

In one embodiment, the ligand binding domain of the CAR is specific for an epitope in the EMPD segment comprising EMPD amino acids 1-17, GLAGGSAQSQRAP-DRVL (SEQ ID NO: 3). In another embodiment, the CAR the ligand binding domain is specific for an epitope in the EMPD segment comprising EMPD amino acids 19-38, HSGQQQGLPRAAGGSVPHPR (SEQ ID NO: 4). Other peptide epitopes that may be targeted include the EMPD segment comprising EMPD amino acids 45-52, RADWPGPP (SEQ ID NO: 5), which has previously been used for generating EMPD-specific antibodies.

Hybridomas clones that secrete mAbs specific for EMPD may be generated, for example, according to the procedure of U.S. Pat. No. 8,460,664, particularly Example 1 thereof. The entire disclosure of U.S. Pat. No. 8,460,664 is incorporated herein by reference. Briefly, mice, e.g. BALB/c mice are immunized subcutaneously with immunogen capable of generating EMPD-specific antibodies, contained in a suitable adjuvant, followed by boosting doses. Following final boost, cells spleen cells are harvested and washed with serum-free DMEM medium and fused with an appropriate immortalized fusion partner cell line, such as NS0 cells. Fused cells are resuspended in HAT medium. Hybridoma supernatants are then screen for antibody binding EMPD by, for example, enzyme-linked immunosorbent assay (ELISA).

In other embodiments, a display library, such as a yeast display library, may be used to generate a large number of EMPD-targeting peptides.

In some embodiments, a non-human antibody, fragment or scFv is humanized, where specific amino acid sequences or regions of the antibody are modified to increase similarity to an antibody naturally produced in a human. Humanized forms of non-human, e.g., murine, antibodies are chimeric immunoglobulins, chains or fragments which contain minimal non-human immunoglobulin elements. Methods of humanizing antibodies are summarized in US Pat. Pub. 2014/0286973 and include, for example, CDR-grafting (see, e.g., European Patent No. EP 239,400; International Publication No. WO 91/09967; and U.S. Pat. Nos. 5,225,539, 5,530,101, and 5,585,089); "veneering" or "resurfacing" (see, e.g., European Patent Nos. EP 592,106 and EP 519, 596; Padlan, 1991, *Molecular Immunology*, 28(4/5):489-498; Studnicka et al., 1994, *Protein Engineering*, 7(6):805-814; and Roguska et al., 1994, *PNAS*, 91:969-973); "chain shuffling" (see, e.g., U.S. Pat. No. 5,565,332; and the various techniques disclosed in, e.g., U.S. Patent Application Publication No. US2005/0042664, U.S. Patent Application Publication No. US2005/0048617, U.S. Pat. Nos. 6,407,213, 5,766,886, International Publication No. WO 9317105, Tan et al., *J. Immunol.*, 169:1119-25 (2002), Caldas et al., *Protein Eng.*, 13(5):353-60 (2000), Morea et al., *Methods*, 20(3):267-79 (2000), Baca et al., *J. Biol. Chem.*, 272(16): 10678-84 (1997), Roguska et al., *Protein Eng.*, 9(10):895-904 (1996), Couto et al., *Cancer Res.*, 55 (23 Supp):5973s-5977s (1995), Couto et al., *Cancer Res.*, 55(8):1717-22 (1995), Sandhu, *Gene*, 150(2):409-10 (1994), and Pedersen et al., *J. Mol. Biol.*, 235(3):959-73 (1994). The disclosures of each of the aforementioned documents are incorporated herein by reference in their entireties. For the most part, humanized antibodies and antibody fragments thereof are human immunoglobulins (recipient antibody or antibody fragment) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region residues of the human immunoglobulin are replaced by corresponding non-human residues. A humanized antibody/antibody fragment can comprise residues which are found neither in the recipient antibody nor in the imported CDR or framework sequences. These modifications can further refine and optimize antibody or antibody fragment performance. In general, the humanized antibody or antibody fragment thereof will comprise substantially all of at least one, and typically two, variable domains, in which all or substantially all of the CDR regions correspond to those of a non-human immunoglobulin and all or a significant portion of the FR regions are those of a human immunoglobulin sequence. The humanized antibody or antibody fragment can also comprise at least a portion of an immunoglobulin constant region (Fc), typically that of a human immunoglobulin. See, e.g., Jones et al., *Nature*, 321: 522-525, 1986; Reichmann et al., *Nature*, 332: 323-329, 1988; and Presta, *Curr. Op. Struct. Biol.*, 2: 593-596, 1992, which are incorporated herein by reference in their entireties.

In certain embodiments, the extracellular ligand-binding domain of the EMPD-specific CAR comprises scFvs based on antibodies ID2F11, 2E3E10 or 1C8GB. The scFvs and their component light chain variable region ($V_L$) and heavy chain variable region ($V_H$), taken together with selected linker amino acid sequences, are identified in Table 1, following the Examples below. The $V_L$ and $V_H$ CDRs are also given in Table 1.

According to certain embodiments, the $V_L$ has at least at least about 90%, at least about 91%, at least about 92%, at least about 93%, at least about 94%, at least about 95%, at least about 96%, at least about 97%, at least about 98%, at least about 99%, or 100% amino acid sequence identity to (i) the sequence of amino acids 23 to 136 of SEQ ID NO:7; (ii) the sequence of amino acids 23 to 136 of SEQ ID NO:9; or the sequence of amino acids 23 to 135 of SEQ ID NO:31. In certain embodiments, the $V_H$ has at least about 90%, at least about 91%, at least about 92%, at least about 93%, at least about 94%, at least about 95%, at least about 96%, at least about 97%, at least about 98%, at least about 99%, or 100% amino acid sequence identity to (i) the sequence of amino acids 152 to 275 of SEQ ID NO:7; (ii) the sequence of amino acids 152 to 270 of SEQ ID NO:9; or the sequence of amino acids 151 to 268 of SEQ ID NO:31.

In certain embodiments, the $V_L$ and $V_H$ CDRs comprises an amino acid sequence of a CDR from Table 1, where, except for the $V_L$ CDR2s (Trp-Ala-Ser and Leu-Val-Ser), from 1 to 3, from 1 to 2, or 1, amino acid is substituted with another amino acid. Preferably, the substitution is a "conservative" amino acid substitution, as that term is understood by those skilled in the art.

Often, framework residues in the framework regions will be substituted with the corresponding residue from the CDR donor antibody to alter, for example improve, antigen binding. These framework substitutions are identified by methods well-known in the art, e.g., by modeling of the interactions of the CDR and framework residues to identify framework residues important for antigen binding and sequence comparison to identify unusual framework residues at particular positions. See, e.g., U.S. Pat. No. 5,585, 089; and Riechmann et al., 1988, *Nature*, 332:323, which are incorporated herein by reference in their entireties.

Intracellular Domain

The CAR includes an intracellular domain that mediates T cell activation upon binding of EMPD to the CAR ligand-binding extracellular domain. An intracellular domain that "mediates T cell activation" is a domain that functions in (i) transducing the primary activation signal to the T cell, or (ii) in transducing a co-stimulatory signaling response by a T cell (including but not limited to, proliferation), or both (i) and (ii). The intracellular domain may thus comprise a primary signaling domain and/or one or more co-stimulatory domains. The primary signaling domain comprises a functional signaling domain derived from a stimulatory molecule. A "stimulatory molecule," refers to a molecule expressed by a T cell that provides the primary cytoplasmic signaling sequence(s) that regulate activation of the TCR complex in a stimulatory way for at least some aspect of the T cell signaling pathway. The primary signaling domain acts in a stimulatory manner and communicates the primary activation signal to the T cell.

Exemplary primary intracellular signaling domains include those derived from the molecules responsible for primary stimulation. While the entire intracellular signaling domain of the stimulatory molecule may be employed, in generating a primary signaling domain, in many cases it is not necessary to utilize the entire chain of the stimulatory molecule.

A primary signaling domain may comprise, and preferably does comprise, at least one immunoreceptor tyrosine-based activation motif ("ITAM"). For a discussion of ITAM-containing polypeptides, see US Pat. Pub. 2015/0368342, particularly paragraphs 0175-0196 thereof. The entire disclosure of US Pat. Pub. 2015/0368342 is incorporated herein by reference. Examples of suitable ITAM-containing polypeptides include, but are not limited to: DAP12; FcεRIγ; CD3δ; CD3ε, CD3γ; CD3ζ; and CD79A. A preferred ITAM-containing polypeptide is CD3ζ.

An ITAM is $YX_1X_2L/I$, where $X_1$ and $X_2$ are independently any amino acid (SEQ ID NO:10). In some cases, the intracellular signaling domain of a CAR comprises 1, 2, 3, 4, or 5 ITAMs. In some cases, an ITAM is repeated twice in an intracellular signaling domain, where the first and second instances of the ITAM are separated from one another by 6 to 8 amino acids, e.g.: $(YX_1X_2L/I)(X_3)_n(YX_1X_2L/I)$, where n is an integer from 6 to 8, and each of the 6-8 $X_3$ can be any amino acid (SEQ ID NO:11). In some cases, a primary intracellular signaling domain of a CAR comprises one ITAM. In some cases, a primary intracellular signaling domain of a CAR comprises three ITAMs.

In certain embodiments, a primary intracellular signaling domain of the CAR can contain the entire amino acid sequence of an ITAM-containing polypeptide. See US Pat. Pub. 2015/0368342 for a description of the ITAM-containing polypeptides DAP12, FcεRI, CD36, CD3ε, CD3γ, CD3ζ and CD79A, including amino acid sequences of known isoforms, and identification of the contained ITAMs.

In other embodiments, a primary intracellular signaling domain for the CAR of the present invention may comprise an ITAM-containing portion of the corresponding full-length parent ITAM-containing intracellular signaling polypeptide. The ITAM-containing portions suitable as intracellular signaling domains in the CAR of the present invention are described in US Pat. Pub. 2015/0368342. In one embodiment, a primary intracellular signaling domain may comprise the intracellular domain of CD3ζ. In certain embodiments, the CD3ζ intracellular domain comprises SEQ ID NO:12, which is amino acids 448-559 of the CAR shown in the combination of FIGS. 3a and 3b. In certain embodiments, the CD3ζ intracellular domain comprising the amino acid sequence SEQ ID NO:12 is encoded by the nucleotide sequence SEQ ID NO: 47.

In some embodiments, a primary intracellular signaling domain comprises an amino acid sequence having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% amino acid sequence identity to SEQ ID NO:12.

The determination of percent sequence identity between two nucleotide or amino acid sequences can be accomplished using a mathematical algorithm. For example, a mathematical algorithm useful for comparing two sequences is the algorithm of Karlin and Altschul (1990, *Proc. Natl. Acad. Sci. USA* 87:2264-2268), modified as in Karlin and Altschul (1993, *Proc. Natl. Acad. Sci. USA* 90:5873-5877). This algorithm is incorporated into the NBLAST and XBLAST programs of Altschul, et al. (1990) *J. Mol. Biol.* 215:403-410, and can be accessed, for example at the National Center for Biotechnology Information (NCBI) world wide web site having the universal resource locator blast(dot)ncbi(dot)nlm(dot)nih(dot)gov/Blast(dot)cgi.

BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al., 1997, *Nucleic Acids Res.* 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAT) can be used.

In one embodiment, the CAR employed in the present invention comprises a extracellular domain of an EMPD-specific scFv, for mIgE recognition, combined with an intracellular signaling domain comprising at least the intracellular domain of human CD3ζ, (i.e., the entire CD3ζ molecule or at least a portion thereof that contains the intracellular domain thereof), to generate a chimeric protein.

The CAR may optionally further comprise on or more co-stimulatory signaling domains to provide a fully competent activation signal to the T cell on which the CAR is expressed. A costimulatory signaling domain refers to the intracellular portion of a costimulatory molecule. A "costimulatory molecule" refers to the cognate binding partner on a T cell that specifically binds with a costimulatory ligand, thereby mediating a costimulatory response by the T cell, such as, but not limited to, proliferation. A co-stimulatory signaling domain can comprise the entire intracellular portion, or the entire native intracellular signaling domain, of the molecule from which it is derived, or a functional fragment thereof. Thus, in certain embodiments, a co-stimulatory signaling domain of a CAR may comprise at least the signaling (cytoplasmic) domain of one or more co-stimulatory molecules for enhanced T cell signaling. The co-stimulatory molecules are typically receptors. The key attribute of this dual-signaling is to confer greater strength of signaling and persistence to the T cells, resulting in overall greater potency.

A co-stimulatory signaling domain can comprise an intracellular portion of a transmembrane protein. Non-limiting examples of suitable co-stimulatory polypeptides include, but are not limited to, 4-1BB (CD137), CD27, CD28, CD134, and ICOS. A co-stimulatory signaling domain can have a length of from 30-70 amino acids. Larger and smaller co-stimulatory domains are also contemplated, such as from 70-200, or 70-100 amino acids, or even larger.

The co-stimulatory signaling domain is derived, for example, from an intracellular portion of the transmembrane protein 4-1BB. In certain embodiments, the intracellular domain of 4-1BB comprises the amino acid sequence:

```
                                          (SEQ ID NO: 15)
Lys Arg Gly Arg Lys Lys Leu Leu Tyr Ile Phe Lys

Gln Pro Phe Met Arg Pro Val Gln Thr Thr Gln Glu

Glu Asp Gly Cys Ser Cys Arg Phe Pro Glu Glu Glu

Glu Gly Gly Cys Glu Leu.
```

In certain embodiments, the aforementioned 4-1BB intracellular domain amino acid sequence is encoded by the nucleotide sequence:

```
                                          (SEQ ID NO: 16)
AAACGGGGCA GAAAGAAACT CCTGTATATA TTCAAACAAC

CATTTATGAG ACCAGTACAA ACTACTCAAG AGGAAGATGG

CTGTAGCTGC CGATTTCCAG AAGAAGAAGA AGGAGGATGT

GAACTG.
```

In some embodiments, the co-stimulatory signaling domain is derived, for example, from an intracellular portion of the transmembrane protein 4-1BB that comprises the amino acid sequence:

```
                                          (SEQ ID NO: 50)
Arg Phe Ser Val Val Lys Arg Gly Arg Lys Lys Leu

Leu Tyr Ile Phe Lys Gln Pro Phe Met Arg Pro Val

Gln Thr Thr Gln Glu Glu Asp Gly Cys Ser Cys Arg

Phe Pro Glu Glu Glu Glu Gly Gly Cys Glu Leu Arg.
```

In certain embodiments, the aforementioned 4-1BB intracellular domain amino acid sequence of SEQ ID NO: 50 is encoded by the nucleotide sequence:

```
                                          (SEQ ID NO: 51)
CGTTTCTCTG TTGTTAAACG GGGCAGAAAG AAACTCCTGT

ATATATTCAA ACAACCATTT ATGAGACCAG TACAAACTAC

TCAAGAGGAA GATGGCTGTA GCTGCCGATT TCCAGAAGAA

GAAGAAGGAG GATGTGAACT GAGA.
```

The co-stimulatory signaling domain may be derived, for example, from an intracellular portion of the transmembrane protein CD28. In certain embodiments, the intracellular domain of CD28 comprises the amino acid sequence:

```
                                          (SEQ ID NO: 17)
Arg Ser Lys Arg Ser Arg Leu Leu His Ser Asp Tyr

Met Asn Met Thr Pro Arg Arg Pro Gly Pro Thr Arg

Lys His Tyr Gln Pro Tyr Ala Pro Pro Arg Asp Phe

Ala Ala Tyr Arg Ser.
```

In certain embodiments, the aforementioned CD28 amino acid sequence of SEQ ID NO:17 is encoded by the nucleotide sequence:

```
                                          (SEQ ID NO: 18)
AGGAGTAAGA GGAGCAGGCT CCTGCACAGT GACTACATGA

ACATGACTCC CCGCCGCCCC GGGCCCACCC GCAAGCATTA

CCAGCCCTAT GCCCCACCAC GCGACTTCGC AGCCTATCGC

TCC.
```

The co-stimulatory signaling domain may be derived, for example, from an intracellular portion of the transmembrane protein ICOS. In certain embodiments, the intracellular domain of ICOS comprises the amino acid sequence:

```
                                          (SEQ ID NO: 19)
Thr Lys Lys Lys Tyr Ser Ser Ser Val His Asp Pro

Asn Gly Glu Tyr Met Phe Met Arg Ala Val Asn Thr

Ala Lys Lys Ser Arg Leu Thr Asp Val Thr Leu.
```

The co-stimulatory signaling domain may be derived, for example, from an intracellular portion of the transmembrane protein CD134.

```
                                          (SEQ ID NO: 20)
Arg Arg Asp Gln Arg Leu Pro Pro Asp Ala His Lys

Pro Pro Gly Gly Gly Ser Phe Arg Thr Pro Ile Gln

Glu Glu Gln Ala Asp Ala His Ser Thr Leu Ala Lys

Ile.
```

The co-stimulatory signaling domain may be derived, for example, from an intracellular portion of the transmembrane protein CD27. In certain embodiments, the intracellular domain of CD27 comprises the amino acid sequence:

```
                                          (SEQ ID NO: 21)
His Gln Arg Arg Lys Tyr Arg Ser Asn Lys Gly Glu

Ser Pro Val Glu Pro Ala Glu Pro Cys Arg Tyr Ser

Cys Pro Arg Glu Glu Glu Gly Ser Thr Ile Pro Ile

Gln Glu Asp Tyr Arg Lys Pro Glu Pro Ala Cys Ser

Pro.
```

A suitable co-stimulatory signaling domain may comprise an amino acid sequence having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% amino acid sequence identity to any of the co-stimulatory molecule amino acid sequences noted above.

An intracellular domain comprising a primary signaling portion containing an ITAM, and an optional co-stimulatory signaling domain(s), may be combined in any order. Preferably, the co-stimulatory domain(s) are located N-terminal to the primary intracellular signaling domain, and is (are) connected to a transmembrane domain of the CAR directly or via a spacer. The ITAM-containing portion is located C-terminal of the co-stimulatory domain(s), and thus forms the C-terminal region of the CAR.

In certain embodiments, the CAR comprises as co-stimulatory signaling domain the signaling domains of CD28 and/or 4-1BB. The proximity of CD28 and/or 4-1BB to the membrane has been shown to improve CAR surface expression (Geiger et al., *Blood* 2001; 98:2354-2371). The principal signaling portion of the intracellular signaling domain, containing the one or more ITAMs, and optional co-stimulatory signaling domains, e.g. the CD28 and/or 4-1BB domains, may be separated by optional spacers of the type described above.

It has been demonstrated that the CD28 signaling region could be provided in the same construct in series with the TCRζ chain to enhance the activation of human T cells, and in the context of antitumor CAR+ T-cells, enhance tumor cell killing. The addition of costimulatory signaling domains increases the potential of transferred T cells to expand and persist in vivo. CAR+ T cells transferred without prior host immunosuppression have been shown to persist for more than 11 years in humans (Scholler et al., *Sci Transl Med.* 2012; 4(132):132ra53). The cells can persist with a memory phenotype, which allows long term monitoring and elimination of target cells (Kalos et al., *Sci Transl Med.* 2011; 3(95):95ra73). In the context of CARs, the addition of CD28 sequences to CD3 chain-based receptors increases antigen-induced secretion of interleukin-2 (IL-2) and in vitro T-cell expansion, potently enhances T-cell receptor-induced proliferation and differentiation of naive T cells, especially at low T-cell receptor occupancy and enhances the expression of downstream regulators that impact on T-cell proliferation, death, differentiation, and effector functions, for hours or days after the initial T cell-antigen presenting cell (APC) encounter. See Zhong et al., *Molecular Therapy* (2010) 18 2, 413-420. Further addition of the cytoplasmic domain of 4-1BB has been shown to result in enhanced signaling. (Id.).

In one embodiment, the co-stimulatory signaling domain comprises the signaling domains of both CD28 and 4-1BB, in N- to C-terminal orientation. A representative co-stimulatory domain composed of CD28 and 4-1BB signaling domains is the segment of SEQ ID NO:7 comprising the continuous sequence of amino acids from amino acid 359 to 447 of SEQ ID NO:7. That segment is designated as SEQ ID NO:48. A suitable co-stimulatory signaling domain may comprise an amino acid sequence having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% amino acid sequence identity to SEQ ID NO:48. According to certain embodiments, the SEQ ID NO: 48 co-stimulatory domain is encoded by the nucleotide sequence SEQ ID NO: 49.

In certain embodiments, the intracellular domain of a CAR comprises a first intracellular signaling domain (either primary or co-stimulatory), with a second intracellular signaling domain (either primary or co-stimulatory) being located on a separate accessory polypeptide. For example a CAR may comprise a primary intracellular signaling domain with one or more co-stimulatory signaling domains being located on the accessory polypeptide. Alternatively, the CAR may comprise one or more co-stimulatory signaling domains, with the primary intracellular signaling domain being located on the accessory polypeptide. It may be appreciated that other combinations are possible, such as locating a primary intracellular signaling domain and a first co-stimulatory signaling domain on the CAR, with a second co-stimulatory domain being located on the accessory polypeptide. In some embodiments, the set of polypeptides (the CAR and the accessory polypeptide) include a dimerization switch that, upon the presence of a dimerization molecule, can couple the polypeptides to one another. The CAR and the accessory polypeptide each contain a first or second member of a dimer pair, i.e., a dimerizer-binding pair. The pair will dimerize upon exposure to an agent, e.g., a small molecule or light for instance, that induces dimerization. This arrangement thus provides for a regulatable CAR (RCAR), which is regulated by selective introduction of the dimerizer. Examples of configurations of RCARs and their dimerization-binding pair elements are disclosed, for example in US 2015/0368342, US 20016/0096892, and Wu et al., *Science* 350(6258):aab4077-1-4077-10 (2015), the entire disclosure of which are incorporated herein by reference.

Transmembrane Domain; Hinge Region

The CAR may further comprise, C-terminal of the EMPD-binding extracellular domain (or optional linker), a transmembrane domain. The transmembrane domain is disposed between the extracellular domain and the intracellular domain (comprising the primary intracellular signaling domain and/or optional co-stimulatory signaling domain(s)). Any transmembrane domain that provides for insertion of a polypeptide into the cell membrane of a eukaryotic (e.g., mammalian) cell is suitable for use.

In certain embodiments, the extracellular domain may be connected to the intracellular domain via a polypeptide segment comprising an extracellular hinge region, a transmembrane domain, and an intracellular spacer. Such a construction is illustrated in FIGS. 3a and 3b combined, 5a and 5b combined, and 6a and 6b combined. For a description of the construction of CARs see, for example, Shirasu et al. *Anticancer Res.* 2012; 32(6):2377-83, the entire disclosure of which is incorporated herein by reference.

The transmembrane domain, and also the extracellular hinge and intracellular spacer, may be derived either from a natural or from a synthetic source. Where the source is natural, the transmembrane domain, the extracellular hinge region and intracellular spacer may be derived, for example, from any membrane-bound or transmembrane protein, such as the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, or immunoglobulin heavy chain. The extracellular hinge region, transmembrane domain, and intracellular spacer may derive from the same transmembrane protein, or may comprise a combination of elements from different transmembrane proteins.

In one embodiment, the transmembrane domain is the CD3ζ transmembrane domain, and the intracellular signaling domain comprises the intracellular domain of CD3ζ. In another embodiment, the CAR comprises a transmembrane domain other than the native CD3ζ transmembrane domain, and a further spacer domain is incorporated between the transmembrane domain and the CD3ζ intracellular domain.

In one embodiment, the extracellular domain is connected to a CD3ζ component comprising all or a portion of the extracellular domain of CD3ζ, the transmembrane domain of CD3ζ, and the intracellular domain of CD3ζ.

In another embodiment, the transmembrane domain comprises the CD8 transmembrane domain. In certain embodiments, CD8 transmembrane domain comprises the amino acid sequence:

```
                                       (SEQ ID NO: 22)
Ile Tyr Ile Trp Ala Pro Leu Ala Gly Thr Cys Gly

Val Leu Leu Leu Ser Leu Val Ile Thr
```

In certain embodiments, the aforementioned CD8 transmembrane domain amino acid sequence of SEQ ID NO:22 is encoded by the nucleotide sequence SEQ ID NO:23.

```
                                       (SEQ ID NO: 23)
ATCTACATCT GGGCGCCCTT GGCCGGGACT TGTGGGGTCC

TTCTCCTGTC ACTGGTTATC ACC
```

In some embodiments, the CAR comprises an intracellular hinge domain comprising a CD8 hinge domain. In certain embodiments, CD8 hinge domain comprises the amino acid sequence:

```
                                       (SEQ ID NO: 24)
Phe Val Pro Val Phe Leu Pro Ala Lys Pro Thr Thr

Thr Pro Ala Pro Arg Pro Pro Thr Pro Ala Pro Thr

Ile Ala Ser Gln Pro Leu Ser Leu Arg Pro Glu Ala

Cys Arg Pro Ala Ala Gly Gly Ala Val His Thr Arg

Gly Leu Asp Phe Ala Cys Asp
```

In certain embodiments, the aforementioned CD8 hinge domain amino acid sequence of SEQ ID NO:24 is encoded by the nucleotide sequence of SEQ ID NO:25:

```
                                       (SEQ ID NO: 25)
TTCGTGCCGG TCTTCCTGCC AGCGAAGCCC ACCACGACGC

CAGCGCCGCG ACCACCAACA CCGGCGCCCA CGCGTCGCAG

CCCCTGTCCC TGCGCCCAGA GGCGTGCCGG CCAGCAGCAG

GAGGAGCAGT GCATCCACAC GAGGGGGCTG GACTTCGCCT

GTGAT
```

In some embodiments, the CAR comprises an intracellular spacer comprising derived from the intracellular domain of CD8. In some embodiments, the intracellular spacer comprises the amino acid sequence which comprises amino acids 352 to 358 of SEQ ID NO:7. The spacer is derived from the intracellular domain of CD8.

Signal Peptide.

The CAR may optionally and preferably comprise an N-terminal segment comprising a signal peptide. The nucleic acid construct encoding the CAR may contain, a nucleic acid segment encoding the signal sequence at the 5' terminus of the open reading frame (ORF), which signal sequence peptide directs the chimeric protein to the cell surface membrane. Since the signal sequence will be removed from the chimeric protein being processed while being directed to the surface membrane, the particular signal sequence will normally not be critical to the subject invention. In one embodiment, the signal sequence comprises the CD3ζ signal peptide. In certain embodiments, the CD3ζ signal peptide comprises the amino acid sequence SEQ ID NO: 26,

```
                                       (SEQ ID NO: 26)
Met Ala Pro Ala Met Glu Ser Pro Thr Leu Leu Cys

Val Ala Leu Leu Phe Phe Ala Pro Asp Gly Val Leu

Ala,
``` and may be encoded by the nucleotide sequence SEQ ID NO:27:

```
                                       (SEQ ID NO: 27)
ATGGCTCCTG CCATGGAATC CCCTACTCTA CTGTGTGTAG

CCTTACTGTT CTTCGCTCCA GATGGCGTGT TAGCA.
```

In another embodiment, the signal sequence comprises an Ig kappa signal peptide, as shown in FIGS. 3a and 3b. In certain embodiments, the Ig kappa signal peptide comprises the amino acid sequence SEQ ID NO: 28,

```
                                       (SEQ ID NO: 28)
Met Asp Phe Gln Val Gln Ile Phe Ser Phe Leu Leu

Ile Ser Ala Ser Val Ile Met Ser Arg Gly,
``` and may be encoded by the nucleotide sequence SEQ ID NO: 29:

```
                                       (SEQ ID NO: 29)
ATGGATTTTC AGGTGCAGAT TTTCAGCTTC CTGCTAATCA

GTGCCTCAGT CATAATGTCC AGAGGA.
```

The signal peptide is fused to the N-terminus of the extracellular domain, optionally through a spacer domain of the type described above.

The CAR may comprise further optional segments, such as other signaling elements in addition to the primary signaling domain and optional co-stimulatory signaling domains.

The components of CAR are thus arranged according to well-known principles. The architecture of CARs for adoptive immunotherapy of cancer is described, for example, in Shirasu et al. *Anticancer Res.* 2012; 32(6):2377-83, showing the arrangement of extracellular ligand-binding domain, hinge/spacer domain, transmembrane domain, intracellular signaling domain, and co-stimulatory domain(s).

In certain embodiments of the CAR, exemplified in FIGS. 3a and 3b combined, 5a and 5b combined, and 6a and 6b combined, the construction of the CAR is characterized, from N-terminus to C-terminus, as follows: Signal peptide; extracellular ligand-binding domain comprising EMPD-specific scFv containing $V_L$, linker and $V_H$; CD8 hinge, transmembrane and intracellular (spacer) domains); co-stimulatory signaling domain comprising CD28 and 4-1BB signaling domains; and primary intracellular signaling domain comprising CD3ζ intracellular domain.

Linkers/Spacers

Adjacent domains of the CAR may be connected by a linker domain, often referred to as a spacer or spacer domain. The linker is an oligo- or polypeptide, and may contain any variety of amino acid sequences. A linker can be a peptide of between about 2 and about 40 amino acids in length, between about 2 and about 25 amino acids in length, or between about 2 and about 10 amino acids in length. Linkers can be produced by using synthetic, linker-encoding oligonucleotides to couple the proteins. Peptide linkers with a degree of flexibility may be used. The use of small amino acids, such as glycine and alanine, are of use in creating a flexible peptide. The creation of such sequences is routine to those of skill in the art.

In one embodiment, a linker comprises a sequence of glycine and serine residues, e.g. the pentapeptide Gly-Gly-Ser-Gly-Gly (SEQ ID NO: 13). Other linker sequences known to those skilled in the art may be utilized. A representative nucleotide sequence encoding the spacer domain Gly-Gly-Ser-Gly-Gly is GGTGGATCAG GAGGA (SEQ ID NO: 14).

Nucleic Acid Constructs and Vectors

The present invention is also directed to DNA constructs encoding the CAR, where the nucleic acid sequences encoding the extracellular ligand binding domain, intracellular domain comprises signaling components (e.g., primary intracellular signaling domain and/or co-stimulatory signaling domains), and other elements are operably linked. A chimeric construct encoding the various nucleotide sequences encoding the CAR components may be directly synthesized or prepared by well-known molecular biology techniques, from naturally derived or synthetically prepared nucleic acids encoding the components. The chimeric constructs, which encode the CAR of the invention may be prepared using natural sequences. The natural genes may be isolated and manipulated, as appropriate, so as to allow for the proper joining of the various domains. Thus, one may prepare the truncated portion of the sequence by employing polymerase chain reaction (PCR) using appropriate primers which result in deletion of the undesired portions of the gene. Alternatively, one may use primer repair where the sequence of interest may be cloned in an appropriate host. In either case, primers may be employed which result in termini which allow for annealing of the sequences to result in the desired open reading frame encoding the CAR protein. Thus. the sequences may be selected to provide for restriction sites which are blunt-ended. or have complementary overlaps. Preferably, the constructs are prepared by overlapping PCR.

In embodiments of the invention, the nucleic acid sequences for representative CARs containing, in 5'-3' order, an Ig kappa signal peptide; an EMPD-binding extracellular domain; a CD8 component comprising the CD8 hinge, transmembrane domain and intracellular domain; CD28 and 4-1BB signaling domains; and CD3ζ intracellular domain, as shown in FIGS. 3a and 3b combined, 5a and 5b combined, and 6a and 6b combined.

The present invention is also directed to vectors in which the DNA of the invention is inserted. Vectors derived from retroviruses are preferred, as they provide long-term gene transfer since and allow stable integration of a transgene and its propagation in daughter cells. Expression of nucleic acids encoding the CARs of the invention may be achieved using well-known molecular biology techniques by operably linking a nucleic acid encoding the CAR to a promoter, and incorporating the construct into a suitable expression vector. The vectors can be suitable for replication and integration in eukaryotes. Typical cloning vectors contain transcription and translation terminators, initiation sequences, and promoters useful for regulation of the expression of the desired nucleic acid sequence.

As the target cell for CAR expression is a T cell, the expression vector is most preferably a lentivirus. In one embodiment, lentiviral vectors encoding CARs are produced according to current good manufacturing practices using a three-plasmid production approach, as original described by Zuufrey et al., *Nat. Biotechnol.* 15, 871-875 (1997), the entire disclosure of which is incorporated herein by reference. Briefly, to package lentiviruses, 293T human embryonic kidney epithelial cells are transfected with the transfer plasmid encoding the CAR, the multiply deleted packaging plasmid, and the plasmid encoding the envelope glycoprotein VSVg. After 24 hours, the lentiviral vectors are harvested by concentrating the culture supernatant through ultracentrifugation.

The $CAR^+$ T cells of the invention can be generated by introducing a lentiviral vector containing a nucleic acid construct encoding the desired CAR into T cells, such as autologous T cells of a patient to be treated for an IgE-mediated allergic disease. A composition comprising autologous T cells is collected from a patient in need of such treatment. The cells are engineered into $CAR^+$ T cells ex vivo, activated and expanded using the methods described herein and known in the art, and then infused back into the patient. The $CAR^+$ T cells replicate in vivo resulting in persistent immunity against cells expressing mIgE.

T cells for genetic modification to express the CARs are obtained from a subject. Sources and methods for collecting, purifying, processing and storing T cells for genetic modification, are described, for example, in paragraphs 00173-00182 of US2013/0287748 A1. The entire disclosure of US2013/0287748 A1 is incorporated herein by reference. Briefly, T cells can be obtained from peripheral blood mononuclear cells, bone marrow, lymph node tissue, cord blood, thymus tissue, tissue from a site of infection, ascites, pleural effusion, spleen tissue, and tumors. Preferably, T cells are obtained from a unit of blood collected from a subject using any number of techniques known to those skilled in the art. Isolation of T cells may proceed according to procedures known in the art, as described in US2013/0287748 A1. The harvested T cells are then expanded using methods well-known in the art, such as described in US2013/0287748 A1.

According to one embodiment, T-cells are harvested and processed for lentiviral transduction as follows. Patient peripheral blood mononuclear cells are purified and washed in phosphate-buffered saline (PBS) with 1% human serum albumin. Lymphocytes are enriched using magnetic bead depletion of monocytes, according to known methods. Lymphocytes are cultured according to Good Manufacturing Practice regulations as previously described by Levine et al., (1998), *J Hematother* 7:437-448. The cells are expanded ex vivo for 14 days in a serum-free hematopoietic cell medium, e.g., X-VIVO 15 of Lonza Group Ltd. (a chemically defined, serum-free hematopoietic cell medium) supplemented with 10% Normal Human AB Serum, and then processed for reinfusion on day 14 of culturing. The magnetic beads are removed using a magnetic cell separation system. The cells are harvested, washed and resuspended in a Plasmalyte A containing 1% human serum albumin.

The processed T cells are then transduced with lentiviral vectors as described above to generate $CAR^+$ T cells for administration. Transduction is carried out according to known protocols. For example, the cells are transduced with lentiviral vectors by mixing with the concentrated vectors and 8 μg/ml polybrene, spun at 2500 RPM for 90 minutes, and incubating in the 37° C. incubator for 24 hours.

Administration of $CAR^+$ T Cells

The $CAR^+$ T cells are administered to a subject in need of treatment for an IgE-mediated allergic disease, or a subject at risk of developing an IgE-mediated allergic disease. The CAR+ T are able to replicate in vivo, providing long-term persistence that can lead to sustained allergic disease control. The CAR+ T may be administered either alone, or as a pharmaceutical composition in combination with one or more pharmaceutically acceptable carriers, diluents or excipients and/or with other components, such as cytokines or other cell populations. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions are preferably formulated for intravenous administration. Preferably, the T cells comprise autologous T cells that are removed from the subject and engineered ex vivo to express the CAR and administered to the subject.

IgE-mediated allergic diseases that may be treated or prevented according to the present invention include, by way of example and not limitation, allergic asthma, food allergy, atopic dermatitis, allergic rhinitis, allergic rhinoconjunctivitis, chronic urticaria and systematic anaphylaxis.

The CAR+ T cells or pharmaceutical composition thereof may be administered by a route that results in the effective delivery of an effective amount of cells to the patient for pharmacological effect. Administration is typically parenteral. Intravenous administration is the preferred route, using infusion techniques that are commonly known in immunotherapy (see, e.g., Rosenberg et al., *New Eng. J. of Med.* 319:1676, 1988). The quantity of CAR+ T cells and frequency of administration are determined by such factors as the condition of the patient, and the type and severity of the patient's disease, although appropriate dosages may be determined by clinical trials. An "effective amount" is determined by a physician with consideration of individual differences in age, weight, disease state, and disease severity of the patient. Generally, the amount of CAR+ T given in a single dosage will range from about $10^6$ to $10^9$ cells/kg body weight, including all integer values within those ranges. The CAR+ T may be administered multiple times at these dosages. The optimal dosage and treatment regime for a particular patient can readily be determined by one skilled in the art of medicine by monitoring the patient for signs of disease and adjusting the treatment accordingly.

Advantage of the EMPD-Specific CAR

The EMPD-specific CAR of the present invention advantageously satisfies certain critical requirements for Adoptive T Cell Therapy targeting mIgE-expressing cells.

Figure 4A:
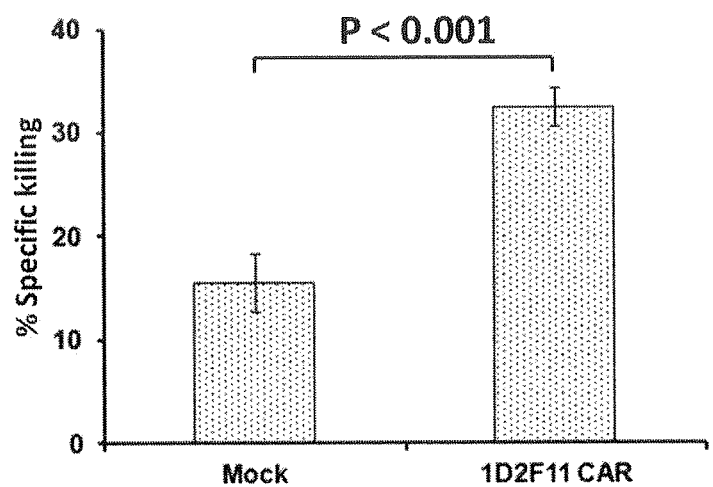
FIG. 4a is a graph of the percentage of specific killing of mIgE-positive U266-luci target cells incubated with primary CD8+ T cells transduced to express an EMPD-specific CAR based on scFv 1D2F11. T cells expressing the 1D2F11 CAR or control T cells (mocked transduced) were incubated with mIgE-positive U266 cells expressing firefly luciferase (U266-luci) at a 1:1 ratio for 16 hours. The percentage of specific killing of the U266-luci cells was calculated based on the luciferase activity in the remaining live U266-luci cells. Specific killing of the T cells expressing the EMPD-specific CAR ("D2F11 CAR") and control mock-transduced T cells ("Mock") is shown.
Figure 4B:
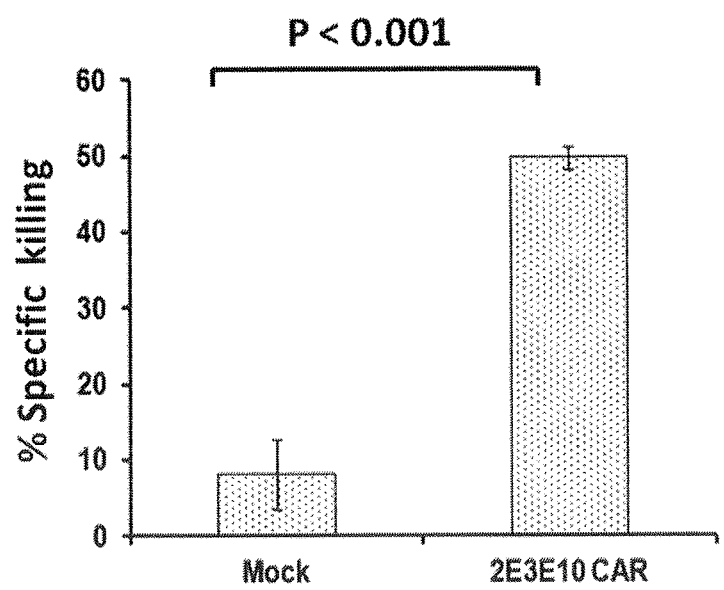
FIG. 4b is a graph of the percentage of specific killing of mIgE-positive U266-luci target cells incubated with primary CD8+ T cells transduced to express an EMPD-specific CAR based on an scFv designated 2E3E10. The killing assay is as described for FIG. 4a. Specific killing of the T cells expressing the EMPD-specific CAR ("2E3E10 CAR") and control mock-transduced T cells ("Mock") is shown.
Figure 4C:
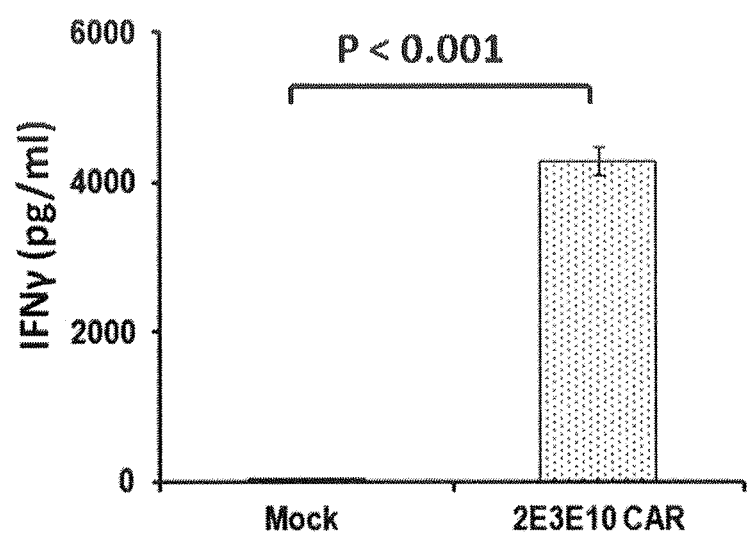
FIG. 4c is a graph of the amount of interferon γ (IFNγ) produced by primary CD8+ T cells transduced to express an EMPD-specific CAR based on scFv 2E3E10 in response to mIgE-positive U266-luci target cells. T cells expressing the 2E3E10 CAR or control T cells (mocked transduced) were incubated with mIgE-positive U266 cells expressing firefly luciferase (U266-luci) at a 1:1 ratio for 16 hours. The concentration of INFγ in the culture supernatant was measured using ELISA (EMPD-specific CAR ("2E3E10 CAR") and control mock-transduced T cells ("Mock")).

The EMPD-specific CAR mediates T cell responses to cells expressing mIgE and causes killing of those cells, as well as T cell cytokine secretion (FIGS. 4a-4c).

IgE may exist on cell surfaces in three different forms: mIgE, soluble IgE bound to FcεRI, and soluble IgE bound to FcεRII. To avoid off-target killing of cells expressing FcεRI and FcεRII that have bound IgE, a CAR directed against IgE-secreting cells should not recognize IgE bound to FcεRI or FcεRII. This goal is achieved by the CAR of the present invention. The EMPD-specific CAR utilized in the practice of the invention would not recognize secreted IgE bound to FcεRI or FcεRII, since EMPD exists only on mIgE, not on secreted IgE.

The majority of B cells express FcεRII and its binding to IgE regulates IgE production (Gould et al., (2003) *Annu Rev Immunol* 21:579-628). FcεRII is also expressed on a variety of inflammatory cells and epithelial cells. It is therefore important that CARs do not mediate off-target T cell responses to these cells though interaction with IgE captured on FcεRII. A CAR directed against IgE-secreting cells should thus not recognize soluble IgE bound to FcεRII on cell surfaces. This goal is achieved by the CAR of the present invention. The EMPD-specificity of the CAR prevents nonspecific targeting of cells with secreted IgE captured on the surface. The EMPD-specific CARs of the invention do not bind IgE that is already bound to FcεRII, preventing CAR+ T cells from targeting FcεRII+ B cells and other cell types such as germinal center follicular dendritic cells.

Thus, it is believed that T cells expressing EMPD-specific CARs of the invention will not target cells expressing FcεRI or FcεRII and cause undesirable side effects in ACT.

It is believed that the effectiveness of the therapy of the present invention, which targets IgE-expressing B-cells, is enhanced by the comparative accessibility of the relevant target cells, as compared to targeting of tumor cells. Tumor cells tend to reside in an immunosuppressive microenvironment. IgE class-switch and affinity maturation takes place in respiratory tract mucosa, suggesting that IgE-expressing B cells and plasma cells originate from mucosal tissues. In the nasal mucosa of patients with rhinitis, about 4% of the B cells and 12-19% of the plasma cells express IgE, whereas IgE expressing plasma cells in the bone marrow are comparably sparse, suggesting that IgE-expressing B cells are concentrated in mucosal tissues. As the first line of defense, mucosal tissues experience frequent infection-related inflammation, which should attract infiltration of T cells, including CAR+ T cells targeting mIgE+ according to the present invention. Moreover, allergic responses mediated by locally produced IgE, e.g., the release of inflammatory mediators by mast cells, should attract the CAR+ T cells to target IgE-expressing cells.

The ACT approach described herein advantageously targets only IgE-expressing B cells, which makes up a very small fraction of total B cells. In normal individuals, serum IgE concentration is 10,000 to 100,000 times lower than IgG (Gould et al. (2003), *Annu Rev Immunol* 21:579-628). It is thus believed that the mIgE-specific approach of the present invention should not significantly impact overall humoral immunity, which is mediated mostly by IgG antibodies.

The practice of the invention is illustrated by the following non-limiting examples.

Example 1

Figure 2:
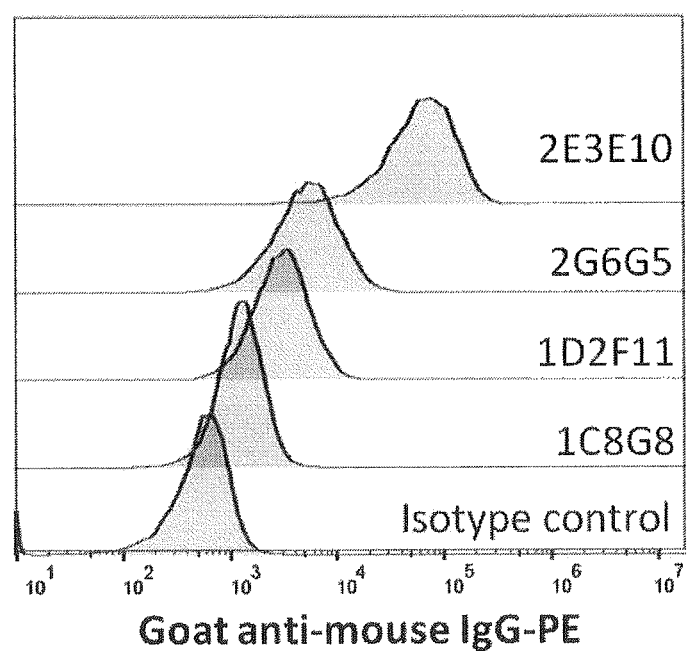
FIG. 2 is a plot of the binding to mIgE-expressing Daudi cells by monoclonal antibodies 1D2F11 and 2E3E10, specific to EMPD amino acid residues 1-17 of SEQ ID NO:2 (GLAGGSAQSQRAPDRVL, SEQ ID NO:3), and monoclonal antibodies 1C8G8 and 2G6G5, specific to EMPD amino acid residues 19-38 of SEQ ID NO: 1 or 2 (HSGQQQGLPRAAGGSVPHPR, SEQ ID NO:4). Following exposure to mAb, the Daudi cells were stained with PE-labeled goat anti-mouse IgG, and analyzed by flow cytometry. An isotype control is included.

EMPD-Specific CAR Based on scFv 1D2F11
A. Hybridoma Generation and Confirmation of Binding Specificity Two hybridoma clones specific to amino acid residues 1-17 of SEQ ID NO: 2 (GLAGGSAQSQRAPDRVL, SEQ ID NO:3) were generated. The clones were designated 1D2F11 and 2E3E10. Two hybridoma clones specific to amino acid residues 19-38 of SEQ ID NO: 1 or 2 (HSGQQQGLPRAAGGSVPHPR, SEQ ID NO:4) were generated. The clones were designated 1C8G8 and 2G6G5. Daudi cells expressing mIgE were stained with monoclonal antibodies 1C8G8, 1D2F11, 2G6G5, or 2E3E10, followed by PE-labeled goat anti-mouse IgG, and analyzed by flow cytometry. An isotype control was included. The results are shown in FIG. 2. All antibodies bound to the mIgE-expressing Daudi cells, at different levels.

B. EMPD-specific CAR based on scFv 1D2F11

Hybridoma clone 1D2F11 was selected for utilization in EMPD-specific CAR production. The variable region of 1D2F11 mAb light chain ($V_L$) and heavy chain ($V_H$) were cloned from the hybridoma by RT-PCR to form scFv for the construction of EMPD-specific CAR according to the protocol of Schaefer et al., *Antibody Engineering* (2010). 21-44. DNA sequences encoding an Ig kappa signal peptide; the scFv; the CD8 hinge, transmembrane domain and intracellular domain; CD28 and 4-1BB signaling domains; and CD3ζ intracellular domain were linked using overlapping PCR and cloned into pLVX, a lentiviral transfer vector. The nucleotide an amino acid sequences of the EMPD-specific CAR based on scFv 1D2F11 is shown in FIGS. 3a and 3b combined. The positions of the various elements-Ig kappa signal peptide; scFv $V_L$; scFv linker; scFv $V_H$; CD8 hinge, transmembrane domain and intracellular domain; CD28 and 4-1BB signaling domains; and CD3ζ intracellular domain—are given in Table 1. The EMPD-specific CAR based on 1D2F11 scFv has the amino acid sequence SEQ ID NO: 7 and is encoded by nucleotide sequence SEQ ID NO:6.

C. T Cell Expression of EMPD-Specific CAR Based on scFv 1D2F11

Primary CD8+ T cells were transduced with the lentivirus encoding the aforementioned elements to produce the CAR based on scFv 1D2F11. T cells expressing the 1D2F11 CAR or control T cells (mocked transduced) were incubated with mIgE-positive U266 cells expressing firefly luciferase (U266-luci) at a 1:1 ratio for 16 hours. The percentage of specific killing of the U266-luci cells was calculated based on the luciferase activity in the remaining live U266-luci cells. The results are shown in FIG. 4a: T cells expressing the 1D2F11 CAR ("1D2F11 CAR"); control mock-transduced T cells ("Mock").

Example 2

EMPD-Specific CAR Based on scFv 2E3E10

Following the procedure of Example 1(B), an EMPD-specific CAR based on scFv from hybridoma clone 2E3E10 was produced. The construction of the CAR is shown in FIGS. 5a and 5b combined: nucleotide sequence (SEQ ID NO: 8); amino acid sequence (SEQ ID NO:9). The positions of the various elements-Ig kappa signal peptide; scFv $V_L$; scFv linker; scFv $V_H$; CD8 hinge, transmembrane domain and intracellular domain; CD28 and 4-1BB signaling domains; and CD3ζ intracellular domain—are given in Table 1.

Following the procedure of Example 1(C), primary CD8+ T cells were transduced with lentivirus encoding the CAR based on scFv 2E3E10. T cells expressing the 2E3E10 CAR or control T cells (mocked transduced) were incubated with mIgE-positive U266 cells expressing firefly luciferase (U266-luci) at a 1:1 ratio for 16 hours. The percentage of specific killing of the U266-luci cells was calculated based on the luciferase activity in the remaining live U266-luci cells. The results are shown in FIG. 4b: T cells expressing the 2E3E10 CAR ("2E3E10 CAR"); control mock-transduced T cells ("Mock").

Primary CD8+ T cells transduced to express an EMPD-specific CAR based on scFv 2E3E10, or control T cells (mocked transduced), were incubated with mIgE-positive U266 cells expressing firefly luciferase (U266-luci) at a 1:1 ratio for 16 hours. The concentration of INFγ in the culture supernatant was measured using ELISA. The results are shown in FIG. 4c: T cells expressing the 2E3E10 CAR ("2E3E10 CAR"); control mock-transduced T cells ("Mock"). Thus, T cells transduced to express EMPD-specific CAR not only lyse mIgE-positive target cells, but also secrete cytokines.

Example 3

EMPD-Specific CAR Based on scFv 1C8GB

Following the procedure of Example 1(B), an EMPD-specific CAR based on scFv from hybridoma clone 1C8 GB is produced. The construction of the CAR is shown in FIGS. 6a and 6b combined: nucleotide sequence (SEQ ID NO:30); amino acid sequence (SEQ ID NO: 31). The positions of the various elements Ig kappa signal peptide; scFv $V_L$; scFv linker; scFv $V_H$; CD8 hinge, transmembrane domain and intracellular domain; CD28 and 4-1BB signaling domains; and CD3ζ intracellular domain—are given in Table 1.

Table 1 identifies the component features of the EMPD-specific CARs of Example 1 (SEQ ID NO:7), Example 2 (SEQ ID NO:9) and Example 3 (SEQ ID NO:31). Numbering in Table 1 refers to amino acid positions in the respective polypeptides of SEQ ID NOs: 7, 9, and 31.

TABLE 1

Features of EMPD-specific CARs by Amino Acid Position

| Feature | EMPD-specific CAR based on scFv 1D2F11 (Ex. 1; FIGS. 3a and 3b; SEQ ID NO: 7) | EMPD-specific CAR based on scFv 2E3E10 (Ex. 2; FIGS. 5a and 5b; SEQ ID NO: 9) | EMPD-specific CAR based on scFv 1C8GB (Ex. 3; FIGS. 6a and 6b; SEQ ID NO: 31) |
|---|---|---|---|
| Igκ signal peptide | 1-22 (SEQ ID NO: 28) | 1-22 (SEQ ID NO: 28) | 1-22 (SEQ ID NO: 28) |
| $V_L$ | 23-136 | 23-136 | 23-135 |
| $V_L$ CDR1 | 49-60 (SEQ ID NO: 32) | 49-60 (SEQ ID NO: 37) | 49-60 (SEQ ID NO: 42) |
| $V_L$ CDR2 | 78-80 (Trp-Ala-Ser) | 78-80 (Trp-Ala-Ser) | 77-79 (Leu-Val-Ser) |
| $V_L$ CDR3 | 117-125 (SEQ ID NO: 33) | 117-125 (SEQ ID NO: 38) | 116-124 (SEQ ID NO: 43) |
| Linker | 137-151 | 137-151 | 136-150 |
| $V_H$ | 152-275 | 152-270 | 151-268 |
| $V_H$ CDR1 | 177-184 (SEQ ID NO: 34) | 177-185 (SEQ ID NO: 39) | 176-184 (SEQ ID NO: 44) |
| $V_H$ CDR2 | 202-209 (SEQ ID NO: 35) | 203-209 (SEQ ID NO: 40) | 202-208 (SEQ ID NO: 45) |
| $V_H$ CDR3 | 248-261 (SEQ ID NO: 36) | 248-256 (SEQ ID NO: 41) | 247-254 (SEQ ID NO: 46) |
| CD8 hinge | 276-330 | 271-325 | 269-324 |
| CD8 trans-membrane domain | 331-351 | 326-346 | 325-344 |
| CD8 intracellular | 352-358 | 347-353 | 345-351 |

The disclosures of each and every patent, patent application, GenBank record, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope used in the practice of the invention. The appended claims are intended to be construed to include all such embodiments and equivalent variations.

I claim:

1. An EMPD-specific chimeric antigen receptor comprising an extracellular ligand binding domain capable of binding an epitope of membrane-bound IgE extracellular membrane-proximal domain (EMPD), a transmembrane domain, and an intracellular domain that mediates T cell activation upon binding of EMPD to the extracellular ligand binding domain, wherein:
 (1) the extracellular ligand binding domain comprises a single chain Fv fragment comprising a light chain variable region comprising the complementarity determining regions SEQ ID NO: 37, Trp-Ala-Ser, and SEQ ID NO: 38, and a heavy chain variable region comprising the complementarity determining regions SEQ ID NO: 39, SEQ ID NO: 40, and SEQ ID NO: 41, said variable light chain and variable heavy chain being connected by a sequence of amino acids forming a flexible linker;
 (2) the transmembrane domain comprises the amino acid sequence of SEQ ID NO: 22; and
 (3) the intracellular domain comprises the amino acid sequence of SEQ ID NO: 50 and the amino acid sequence of SEQ ID NO: 12.

2. The EMPD-specific chimeric antigen receptor of claim 1, wherein the intracellular domain further comprises a costimulatory signaling domain comprising at least one amino acid sequence selected from the group of SEQ ID NO: 21, SEQ ID NO: 17, SEQ ID NO: 20, and SEQ ID NO: 19.

3. The EMPD-specific chimeric antigen receptor of claim 2, wherein the costimulatory signaling domain comprises the amino acid sequence SEQ ID NO: 17.

4. The EMPD-specific chimeric antigen receptor of claim 1 comprising an amino acid sequence selected from the group of amino sequences consisting of:
 (a) SEQ ID NO:9; and
 (b) the sequence of amino acids from amino acid 23 to amino acid 554 of SEQ ID NO:9.

5. An isolated nucleic acid sequence encoding the EMPD-specific chimeric antigen receptor of claim 1.

6. The isolated nucleic acid according to claim 5, wherein the encoded intracellular domain further comprises a costimulatory signaling domain comprising at least one amino acid sequence selected from the group of SEQ ID NO: 21, SEQ ID NO: 17, SEQ ID NO: 20, and SEQ ID NO: 19.

7. The isolated nucleic acid according to claim 6, wherein the encoded costimulatory signaling domain comprises the amino acid sequence SEQ ID NO: 17.

8. The isolated nucleic acid according to claim 5, wherein the EMPD-specific chimeric antigen receptor comprises an amino acid sequence selected from the group of amino sequences consisting of:
 (a) SEQ ID NO: 9; and
 (b) the sequence of amino acids from amino acid 23 to amino acid 554 of SEQ ID NO: 9.

9. The isolated nucleic acid sequence according to claim 8, comprising a nucleic acid sequence selected from the group consisting of:
 (a) SEQ ID NO: 8; and
 (b) the sequence of nucleotides from nucleotide 67 to nucleotide 1662 of SEQ ID NO: 8.

10. A vector comprising a nucleic acid sequence encoding the EMPD-specific chimeric antigen receptor of claim 1.

11. The vector according to claim 10, wherein the EMPD-specific chimeric antigen receptor comprises an amino acid sequence selected from the group of amino sequences consisting of:
 (a) SEQ ID NO: 9; and
 (b) the sequence of amino acids from amino acid 23 to amino acid 554 of SEQ ID NO: 9.

12. The vector according to claim 11, comprising a nucleic acid sequence selected from the group consisting of:
 (a) SEQ ID NO: 8; and
 (b) the sequence of nucleotides from nucleotide 67 to nucleotide 1662 of SEQ ID NO: 8.

13. A T cell comprising a nucleic acid sequence encoding the EMPD-specific chimeric antigen receptor of claim 1.

14. A T cell expressing the EMPD-specific chimeric antigen receptor of claim 1.

15. The T cell of claim 14, wherein the intracellular domain further comprises a costimulatory signaling domain comprising at least one amino acid sequence selected from the group of SEQ ID NO: 21, SEQ ID NO: 17, SEQ ID NO: 20, and SEQ ID NO: 19.

16. The T cell of claim 15, wherein the costimulatory signaling domain comprises the amino acid sequence SEQ ID NO: 17.

17. An EMPD-binding antibody or antigen binding fragment thereof comprising a light chain variable region the complementarity determining regions SEQ ID NO: 37, Trp-Ala-Ser, and SEQ ID NO: 38, and a heavy chain variable region comprising the complementarity determining regions SEQ ID NO: 39, SEQ ID NO: 40, and SEQ ID NO: 41.

18. The T cell of claim 14, wherein the EMPD-specific chimeric antigen receptor comprises an amino acid sequence selected from the group of amino sequences consisting of:
 (a) SEQ ID NO:9; and
 (b) the sequence of amino acids from amino acid 23 to amino acid 554 of SEQ ID NO: 9.

19. The EMPD-binding antibody or antigen binding fragment thereof of claim 17, wherein the antibody or antigen binding fragment thereof is humanized.

20. The EMPD-binding antibody or antigen binding fragment thereof of claim 17, wherein said antibody or antigen binding fragment thereof is an scFv and said variable light chain and variable heavy chain are connected by a sequence of amino acids forming a flexible linker.

21. An isolated nucleic acid sequence encoding the EMPD-binding antibody or antigen binding fragment thereof of claim 17.

22. An isolated nucleic acid sequence encoding the EMPD-binding antibody or antigen binding fragment thereof of claim 19.

23. A host cell expressing the EMPD-binding antibody or antigen binding fragment thereof of claim 20.

24. A fusion polypeptide comprising the EMPD-binding antibody or antigen binding fragment thereof of claim 17 and a second polypeptide.

25. An isolated nucleic acid sequence encoding the fusion polypeptide of claim 24.

26. A host cell expressing the fusion polypeptide of claim 24.

* * * * *

SEQUENCE LISTING

```
<160> NUMBER OF SEQ ID NOS: 51

<210> SEQ ID NO 1
<211> LENGTH: 52
<212> TYPE: PRT
<213> ORGANISM: Homo sapiens

<400> SEQUENCE: 1

Gly Leu Ala Gly Gly Ser Ala Gln Ser Gln Arg Ala Pro Asp Arg Leu
1               5                   10                  15

Leu Cys His Ser Gly Gln Gln Gln Gly Leu Pro Arg Ala Ala Gly Gly
            20                  25                  30

Ser Val Pro His Pro Arg Cys His Cys Gly Ala Gly Arg Ala Asp Trp
        35                  40                  45

Pro Gly Pro Pro
    50

<210> SEQ ID NO 2
<211> LENGTH: 52
<212> TYPE: PRT
<213> ORGANISM: Homo sapiens

<400> SEQUENCE: 2

Gly Leu Ala Gly Gly Ser Ala Gln Ser Gln Arg Ala Pro Asp Arg Val
1               5                   10                  15

Leu Cys His Ser Gly Gln Gln Gln Gly Leu Pro Arg Ala Ala Gly Gly
            20                  25                  30

Ser Val Pro His Pro Arg Cys His Cys Gly Ala Gly Arg Ala Asp Trp
        35                  40                  45

Pro Gly Pro Pro
    50

<210> SEQ ID NO 3
<211> LENGTH: 17
<212> TYPE: PRT
<213> ORGANISM: Homo sapiens

<400> SEQUENCE: 3

Gly Leu Ala Gly Gly Ser Ala Gln Ser Gln Arg Ala Pro Asp Arg Val
1               5                   10                  15

Leu

<210> SEQ ID NO 4
<211> LENGTH: 20
<212> TYPE: PRT
<213> ORGANISM: Homo sapiens

<400> SEQUENCE: 4

His Ser Gly Gln Gln Gln Gly Leu Pro Arg Ala Ala Gly Gly Ser Val
1               5                   10                  15

Pro His Pro Arg
            20
```

```
<210> SEQ ID NO 5
<211> LENGTH: 8
<212> TYPE: PRT
<213> ORGANISM: Homo sapiens

<400> SEQUENCE: 5

Arg Ala Asp Trp Pro Gly Pro Pro
1               5

<210> SEQ ID NO 6
<211> LENGTH: 1677
<212> TYPE: DNA
<213> ORGANISM: Artificial Sequence
<220> FEATURE:
<223> OTHER INFORMATION: Synthesized, encoding EMPD-specific chimeric
      antigen receptor

<400> SEQUENCE: 6
atggattttc aggtgcagat tttcagcttc ctgctaatca gtgcctcagt cataatgtcc      60
agaggagaca ttgtgatgtc acagtctcca tcctccctag ctgtgtcagt ggagagaag     120 gttactatga gctgcaagtc cagtcagagc cttttatata gtagcaatca aaagaactac    180
ttggcctggt accagcagaa accagggcag tctcctaaac tgctgattta ctgggcatcc    240
actagggaat ctggggtccc tgatcgcttc acaggcagtg gatctgggac agatttcact    300
ctcaccatca gcagtgtgaa ggctgaagac ctggcagttt attactgtca gcaatattat    360
agctatccgt acacgttcgg aggggggacc aagctggaaa taaaacgggg gtctacatct    420
ggatctggga gccgggttc tggtgaggt tctgaggttc agctgcagca gtctgggact    480
gtgctggcaa ggccggggc ttccgtgaag atgtcctgca aggcttctgg ctacagcttt    540
accagccact ggatgcactg ggtaaaacag aggcctggac agggtctaga atggattggt    600
gctatttatc ctggaaatag tgatactatc tacaaccaga agttcaaggg caaggccaaa    660
ctgactgcag tcacatccgc cagcactgcc tacatggagc tcagcagcct gacaaatgag    720
gactctgcgg tctattactg tacaagatgg agggatgaca actacgacta tgatatggac    780
tactggggtc aaggaacctc agtcaccgtc tcctcagcgg ccgcattcgt gccggtcttc    840
ctgccagcga agcccaccac gacgccagcg ccgcgaccac caacaccggc gcccaccatc    900
gcgtcgcagc ccctgtccct gcgcccagag gcgtgccggc cagcagcagg aggagcagtg    960
cacacgaggg ggctggactt cgcctgtgat atctacatct gggcgccctt ggccgggact   1020 tgtgggtcc ttctcctgtc actggttatc accctttact gcaaccacag gaacaggagt   1080
aagaggagca ggctcctgca cagtgactac atgaacatga ctccccgcgc ccccgggccc   1140
acccgcaagc attaccagcc ctatgcccca ccacgcgact tcgcagccta tcgctcccgt   1200
ttctctgttg ttaaacgggg cagaaagaag ctcctgtata tattcaaaca accatttatg   1260
agaccagtac aaactactca agaggaagat ggctgtagct gccgatttcc agaagaagaa   1320
gaaggaggat gtgaactgag agtgaagttc agcaggagcg cagacgcccc cgcgtaccag   1380
cagggccaga accagctcta taacgagctc aatctaggac gaagagagga gtacgatgtt   1440
ttggacaaga gacgtggccg ggaccctgag atgggggaa agccgcagag aaggaagaac   1500
cctcaggaag gcctgtacaa tgaactgcag aaagataaga tggcggaggc ctacagtgag   1560
attgggatga aggcgagcg ccggaggggc aaggggcacg atggccttta ccagggtctc   1620
agtacagcca ccaaggacac ctacgacgcc cttcacatgc aggccctgcc ccctcgc      1677
```

<210> SEQ ID NO 7
<211> LENGTH: 559
<212> TYPE: PRT
<213> ORGANISM: Artificial Sequence
<220> FEATURE:
<223> OTHER INFORMATION: Synthesized EMPD-specific chimeric antigen receptor

<400> SEQUENCE: 7

```
Met Asp Phe Gln Val Gln Ile Phe Ser Phe Leu Leu Ile Ser Ala Ser
1               5                   10                  15

Val Ile Met Ser Arg Gly Asp Ile Val Met Ser Gln Ser Pro Ser Ser
                20                  25                  30

Leu Ala Val Ser Val Gly Glu Lys Val Thr Met Ser Cys Lys Ser Ser
            35                  40                  45

Gln Ser Leu Leu Tyr Ser Ser Asn Gln Lys Asn Tyr Leu Ala Trp Tyr
        50                  55                  60

Gln Gln Lys Pro Gly Gln Ser Pro Lys Leu Leu Ile Tyr Trp Ala Ser
65                  70                  75                  80

Thr Arg Glu Ser Gly Val Pro Asp Arg Phe Thr Gly Ser Gly Ser Gly
                85                  90                  95

Thr Asp Phe Thr Leu Thr Ile Ser Ser Val Lys Ala Glu Asp Leu Ala
            100                 105                 110

Val Tyr Tyr Cys Gln Gln Tyr Tyr Ser Tyr Pro Tyr Thr Phe Gly Gly
        115                 120                 125

Gly Thr Lys Leu Glu Ile Lys Arg Gly Ser Thr Ser Gly Ser Gly Lys
    130                 135                 140

Pro Gly Ser Gly Glu Gly Ser Glu Val Gln Leu Gln Gln Ser Gly Thr
145                 150                 155                 160

Val Leu Ala Arg Pro Gly Ala Ser Val Lys Met Ser Cys Lys Ala Ser
                165                 170                 175

Gly Tyr Ser Phe Thr Ser His Trp Met His Trp Val Lys Gln Arg Pro
            180                 185                 190

Gly Gln Gly Leu Glu Trp Ile Gly Ala Ile Tyr Pro Gly Asn Ser Asp
        195                 200                 205

Thr Ile Tyr Asn Gln Lys Phe Lys Gly Lys Ala Lys Leu Thr Ala Val
    210                 215                 220

Thr Ser Ala Ser Thr Ala Tyr Met Glu Leu Ser Ser Leu Thr Asn Glu
225                 230                 235                 240

Asp Ser Ala Val Tyr Tyr Cys Thr Arg Trp Arg Asp Asp Asn Tyr Asp
                245                 250                 255

Tyr Asp Met Asp Tyr Trp Gly Gln Gly Thr Ser Val Thr Val Ser Ser
            260                 265                 270

Ala Ala Ala Phe Val Pro Val Phe Leu Pro Ala Lys Pro Thr Thr Thr
        275                 280                 285

Pro Ala Pro Arg Pro Pro Thr Pro Ala Pro Thr Ile Ala Ser Gln Pro
    290                 295                 300

Leu Ser Leu Arg Pro Glu Ala Cys Arg Pro Ala Ala Gly Gly Ala Val
305                 310                 315                 320

His Thr Arg Gly Leu Asp Phe Ala Cys Asp Ile Tyr Ile Trp Ala Pro
                325                 330                 335

Leu Ala Gly Thr Cys Gly Val Leu Leu Leu Ser Leu Val Ile Thr Leu
            340                 345                 350

Tyr Cys Asn His Arg Asn Arg Ser Lys Arg Ser Arg Leu Leu His Ser
        355                 360                 365
```

Asp Tyr Met Asn Met Thr Pro Arg Arg Pro Gly Pro Thr Arg Lys His
370                 375                 380

Tyr Gln Pro Tyr Ala Pro Pro Arg Asp Phe Ala Ala Tyr Arg Ser Arg
385                 390                 395                 400

Phe Ser Val Val Lys Arg Gly Arg Lys Lys Leu Leu Tyr Ile Phe Lys
                405                 410                 415

Gln Pro Phe Met Arg Pro Val Gln Thr Thr Gln Glu Glu Asp Gly Cys
                420                 425                 430

Ser Cys Arg Phe Pro Glu Glu Glu Glu Gly Gly Cys Glu Leu Arg Val
            435                 440                 445

Lys Phe Ser Arg Ser Ala Asp Ala Pro Ala Tyr Gln Gln Gly Gln Asn
        450                 455                 460

Gln Leu Tyr Asn Glu Leu Asn Leu Gly Arg Arg Glu Glu Tyr Asp Val
465                 470                 475                 480

Leu Asp Lys Arg Arg Gly Arg Asp Pro Glu Met Gly Gly Lys Pro Gln
                485                 490                 495

Arg Arg Lys Asn Pro Gln Glu Gly Leu Tyr Asn Glu Leu Gln Lys Asp
                500                 505                 510

Lys Met Ala Glu Ala Tyr Ser Glu Ile Gly Met Lys Gly Glu Arg Arg
            515                 520                 525

Arg Gly Lys Gly His Asp Gly Leu Tyr Gln Gly Leu Ser Thr Ala Thr
        530                 535                 540

Lys Asp Thr Tyr Asp Ala Leu His Met Gln Ala Leu Pro Pro Arg
545                 550                 555

<210> SEQ ID NO 8
<211> LENGTH: 1662
<212> TYPE: DNA
<213> ORGANISM: Artificial Sequence
<220> FEATURE:
<223> OTHER INFORMATION: Synthesized, encoding EMPD-specific chimeric
      antigen receptor

<400> SEQUENCE: 8 atggatttc aggtgcagat tttcagcttc ctgctaatca gtgcctcagt cataatgtcc      60
agaggagaca ttgtgatgtc acagtctcca tcctccctag ctgtgtcagt ggagagaag    120 gttactatga gctgcaagtc cagtcagagc cttttatata gtagcaatca aaagaactac   180
ttggcctggt accagcagaa accagggcag tctcctaaac tgctgattta ctgggcatcc   240
actagggaat ctggggtccc tgatcgcttc acaggcagtg gatctgggac agatttcact   300
ctcaccatca gcagtgtgaa ggctgaagac ctggcagttt attactgtca gcaatattat   360
agctatccgt ggacgttcgg tggaggcacc aagctggaaa tcaaacgggg gtctacatct   420
ggatctggga gccgggttc tggtgagggt tctgatgtac agcttcagga gtcaggacct   480
ggcctcgtga aaccttctca gtctctgtct ctcacctgct ctgtcactgg ctactccatc   540
accagtggtt attactggaa ctggatccgg cagtttccag gtaacaaact ggaatggatg   600
ggctccataa gctacgacgg tagcaataac tacaacccat ctctcaaaaa tcgaatctcc   660
atcactcgtg acacatctaa gaaccagttt ttcctgaagt tgaattctgt gactactgag   720
gacacagcta catattactg tgcaagagac tacgggggct tgactactg gggccaaggc   780 accactctca cagtctcctc agcggccgca ttcgtgccgg tcttcctgcc agcgaagccc   840
accacgacgc cagcgccgcg accaccaaca ccggcgccca ccatcgcgtc gcagcccctg   900
tccctgcgcc cagaggcgtg ccggccagca gcaggaggag cagtgcacac gagggggctg   960

```
gacttcgcct gtgatatcta catctgggcg cccttggccg ggacttgtgg ggtccttctc    1020
ctgtcactgg ttatcaccct ttactgcaac cacaggaaca ggagtaagag gagcaggctc    1080
ctgcacagtg actacatgaa catgactccc cgccgccccg ggcccacccg caagcattac    1140
cagccctatg ccccaccacg cgacttcgca gcctatcgct cccgtttctc tgttgttaaa    1200
cggggcagaa agaagctcct gtatatattc aaacaaccat ttatgagacc agtacaaact    1260
actcaagagg aagatggctg tagctgccga tttccagaag aagaagaagg aggatgtgaa    1320
ctgagagtga agttcagcag gagcgcagac gcccccgcgt accagcaggg ccagaaccag    1380
ctctataacg agctcaatct aggacgaaga gaggagtacg atgttttgga caagagacgt    1440
ggccgggacc ctgagatggg gggaaagccg cagagaagga agaaccctca ggaaggcctg    1500
tacaatgaac tgcagaaaga taagatggcg gaggcctaca gtgagattgg gatgaaaggc    1560
gagcgccgga ggggcaaggg gcacgatggc ctttaccagg gtctcagtac agccaccaag    1620
gacacctacg acgcccttca catgcaggcc ctgccccctc gc                       1662
```

<210> SEQ ID NO 9
<211> LENGTH: 554
<212> TYPE: PRT
<213> ORGANISM: Artificial Sequence
<220> FEATURE:
<223> OTHER INFORMATION: Synthesized EMPD-specific chimeric antigen
      receptor

<400> SEQUENCE: 9

```
Met Asp Phe Gln Val Gln Ile Phe Ser Phe Leu Leu Ile Ser Ala Ser
1               5                   10                  15

Val Ile Met Ser Arg Gly Asp Ile Val Met Ser Gln Ser Pro Ser Ser
            20                  25                  30

Leu Ala Val Ser Val Gly Glu Lys Val Thr Met Ser Cys Lys Ser Ser
        35                  40                  45

Gln Ser Leu Leu Tyr Ser Ser Asn Gln Lys Asn Tyr Leu Ala Trp Tyr
    50                  55                  60

Gln Gln Lys Pro Gly Gln Ser Pro Lys Leu Leu Ile Tyr Trp Ala Ser
65                  70                  75                  80

Thr Arg Glu Ser Gly Val Pro Asp Arg Phe Thr Gly Ser Gly Ser Gly
                85                  90                  95

Thr Asp Phe Thr Leu Thr Ile Ser Ser Val Lys Ala Glu Asp Leu Ala
            100                 105                 110

Val Tyr Tyr Cys Gln Gln Tyr Tyr Ser Tyr Pro Trp Thr Phe Gly Gly
        115                 120                 125

Gly Thr Lys Leu Glu Ile Lys Arg Gly Ser Thr Ser Gly Ser Gly Lys
    130                 135                 140

Pro Gly Ser Gly Glu Gly Ser Asp Val Gln Leu Gln Glu Ser Gly Pro
145                 150                 155                 160

Gly Leu Val Lys Pro Ser Gln Ser Leu Ser Leu Thr Cys Ser Val Thr
                165                 170                 175

Gly Tyr Ser Ile Thr Ser Gly Tyr Tyr Trp Asn Trp Ile Arg Gln Phe
            180                 185                 190

Pro Gly Asn Lys Leu Glu Trp Met Gly Ser Ile Ser Tyr Asp Gly Ser
        195                 200                 205

Asn Asn Tyr Asn Pro Ser Leu Lys Asn Arg Ile Ser Ile Thr Arg Asp
    210                 215                 220

Thr Ser Lys Asn Gln Phe Phe Leu Lys Leu Asn Ser Val Thr Thr Glu
225                 230                 235                 240
```

```
Asp Thr Ala Thr Tyr Tyr Cys Ala Arg Asp Tyr Gly Gly Phe Asp Tyr
                245                 250                 255

Trp Gly Gln Gly Thr Thr Leu Thr Val Ser Ser Ala Ala Ala Phe Val
            260                 265                 270

Pro Val Phe Leu Pro Ala Lys Pro Thr Thr Thr Pro Ala Pro Arg Pro
        275                 280                 285

Pro Thr Pro Ala Pro Thr Ile Ala Ser Gln Pro Leu Ser Leu Arg Pro
    290                 295                 300

Glu Ala Cys Arg Pro Ala Ala Gly Gly Ala Val His Thr Arg Gly Leu
305                 310                 315                 320

Asp Phe Ala Cys Asp Ile Tyr Ile Trp Ala Pro Leu Ala Gly Thr Cys
                325                 330                 335

Gly Val Leu Leu Leu Ser Leu Val Ile Thr Leu Tyr Cys Asn His Arg
            340                 345                 350

Asn Arg Ser Lys Arg Ser Arg Leu Leu His Ser Asp Tyr Met Asn Met
        355                 360                 365

Thr Pro Arg Arg Pro Gly Pro Thr Arg Lys His Tyr Gln Pro Tyr Ala
    370                 375                 380

Pro Pro Arg Asp Phe Ala Ala Tyr Arg Ser Arg Phe Ser Val Val Lys
385                 390                 395                 400

Arg Gly Arg Lys Lys Leu Leu Tyr Ile Phe Lys Gln Pro Phe Met Arg
                405                 410                 415

Pro Val Gln Thr Thr Gln Glu Glu Asp Gly Cys Ser Cys Arg Phe Pro
            420                 425                 430

Glu Glu Glu Glu Gly Gly Cys Glu Leu Arg Val Lys Phe Ser Arg Ser
        435                 440                 445

Ala Asp Ala Pro Ala Tyr Gln Gln Gly Gln Asn Gln Leu Tyr Asn Glu
    450                 455                 460

Leu Asn Leu Gly Arg Arg Glu Glu Tyr Asp Val Leu Asp Lys Arg Arg
465                 470                 475                 480

Gly Arg Asp Pro Glu Met Gly Gly Lys Pro Gln Arg Arg Lys Asn Pro
                485                 490                 495

Gln Glu Gly Leu Tyr Asn Glu Leu Gln Lys Asp Lys Met Ala Glu Ala
            500                 505                 510

Tyr Ser Glu Ile Gly Met Lys Gly Glu Arg Arg Arg Gly Lys Gly His
        515                 520                 525

Asp Gly Leu Tyr Gln Gly Leu Ser Thr Ala Thr Lys Asp Thr Tyr Asp
    530                 535                 540

Ala Leu His Met Gln Ala Leu Pro Pro Arg
545                 550

<210> SEQ ID NO 10
<211> LENGTH: 4
<212> TYPE: PRT
<213> ORGANISM: Artificial Sequence
<220> FEATURE:
<223> OTHER INFORMATION: synthetic polypeptide
<220> FEATURE:
<221> NAME/KEY: MISC_FEATURE
<222> LOCATION: (2)..(3)
<223> OTHER INFORMATION: the amino acids in these positions can be any
      amino acid
<220> FEATURE:
<221> NAME/KEY: MISC_FEATURE
<222> LOCATION: (4)..(4)
<223> OTHER INFORMATION: the amino acid in this position can be either
      Leu or Ile
```

```
<400> SEQUENCE: 10

Tyr Xaa Xaa Xaa
1

<210> SEQ ID NO 11
<211> LENGTH: 16
<212> TYPE: PRT
<213> ORGANISM: Artificial Sequence
<220> FEATURE:
<223> OTHER INFORMATION: synthetic polypeptide
<220> FEATURE:
<221> NAME/KEY: MISC_FEATURE
<222> LOCATION: (2)..(3)
<223> OTHER INFORMATION: the amino acids in these positions can be any
      amino acid
<220> FEATURE:
<221> NAME/KEY: MISC_FEATURE
<222> LOCATION: (4)..(4)
<223> OTHER INFORMATION: the amino acids in this position can be either
      Leu or Ile
<220> FEATURE:
<221> NAME/KEY: MISC_FEATURE
<222> LOCATION: (5)..(10)
<223> OTHER INFORMATION: the amino acids in these positions can be any
      amino acid
<220> FEATURE:
<221> NAME/KEY: MISC_FEATURE
<222> LOCATION: (11)..(12)
<223> OTHER INFORMATION: The amino acids in these positions may be
      present or absent such that either one or two amino acids are
      present.  The amino acids in these positions can be any amino acid
<220> FEATURE:
<221> NAME/KEY: MISC_FEATURE
<222> LOCATION: (14)..(15)
<223> OTHER INFORMATION: the amino acids in these positions can be any
      naturally occurring amino acid
<220> FEATURE:
<221> NAME/KEY: MISC_FEATURE
<222> LOCATION: (16)..(16)
<223> OTHER INFORMATION: the amino acid in this position can be either
      Leu or Ile

<400> SEQUENCE: 11

Tyr Xaa Xaa Xaa Xaa Xaa Xaa Xaa Xaa Xaa Xaa Tyr Xaa Xaa Xaa
1               5                   10                  15

<210> SEQ ID NO 12
<211> LENGTH: 112
<212> TYPE: PRT
<213> ORGANISM: Homo sapiens

<400> SEQUENCE: 12

Val Lys Phe Ser Arg Ser Ala Asp Ala Pro Ala Tyr Gln Gln Gly Gln
1               5                   10                  15

Asn Gln Leu Tyr Asn Glu Leu Asn Leu Gly Arg Arg Glu Glu Tyr Asp
            20                  25                  30

Val Leu Asp Lys Arg Arg Gly Arg Asp Pro Glu Met Gly Gly Lys Pro
        35                  40                  45

Gln Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
                100                 105                 110
```

```
<210> SEQ ID NO 13
<211> LENGTH: 5
<212> TYPE: PRT
<213> ORGANISM: Artificial Sequence
<220> FEATURE:
<223> OTHER INFORMATION: Synthesized linker

<400> SEQUENCE: 13

Gly Gly Ser Gly Gly
1               5

<210> SEQ ID NO 14
<211> LENGTH: 15
<212> TYPE: DNA
<213> ORGANISM: Artificial Sequence
<220> FEATURE:
<223> OTHER INFORMATION: Synthesized linker

<400> SEQUENCE: 14
ggtggatcag gagga                                                     15

<210> SEQ ID NO 15
<211> LENGTH: 42
<212> TYPE: PRT
<213> ORGANISM: Homo sapiens

<400> SEQUENCE: 15

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 16
<211> LENGTH: 126
<212> TYPE: DNA
<213> ORGANISM: Homo sapiens

<400> SEQUENCE: 16
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                             126

<210> SEQ ID NO 17
<211> LENGTH: 41
<212> TYPE: PRT
<213> ORGANISM: Homo sapiens

<400> SEQUENCE: 17

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 18
<211> LENGTH: 123
<212> TYPE: DNA
<213> ORGANISM: Homo sapiens
```

```
<400> SEQUENCE: 18
aggagtaaga ggagcaggct cctgcacagt gactacatga acatgactcc ccgccgcccc    60
gggcccaccc gcaagcatta ccagccctat gccccaccac gcgacttcgc agcctatcgc   120
tcc                                                                 123

<210> SEQ ID NO 19
<211> LENGTH: 35
<212> TYPE: PRT
<213> ORGANISM: Homo sapiens

<400> SEQUENCE: 19

Thr Lys Lys Lys Tyr Ser Ser Ser Val His Asp Pro Asn Gly Glu Tyr
1               5                   10                  15

Met Phe Met Arg Ala Val Asn Thr Ala Lys Lys Ser Arg Leu Thr Asp
            20                  25                  30

Val Thr Leu
        35

<210> SEQ ID NO 20
<211> LENGTH: 37
<212> TYPE: PRT
<213> ORGANISM: Homo sapiens

<400> SEQUENCE: 20

Arg Arg Asp Gln Arg Leu Pro Pro Asp Ala His Lys Pro Pro Gly Gly
1               5                   10                  15

Gly Ser Phe Arg Thr Pro Ile Gln Glu Glu Gln Ala Asp Ala His Ser
            20                  25                  30

Thr Leu Ala Lys Ile
        35

<210> SEQ ID NO 21
<211> LENGTH: 49
<212> TYPE: PRT
<213> ORGANISM: Homo sapiens

<400> SEQUENCE: 21

His Gln Arg Arg Lys Tyr Arg Ser Asn Lys Gly Glu Ser Pro Val Glu
1               5                   10                  15

Pro Ala Glu Pro Cys Arg Tyr Ser Cys Pro Arg Glu Glu Glu Gly Ser
            20                  25                  30

Thr Ile Pro Ile Gln Glu Asp Tyr Arg Lys Pro Glu Pro Ala Cys Ser
        35                  40                  45

Pro

<210> SEQ ID NO 22
<211> LENGTH: 21
<212> TYPE: PRT
<213> ORGANISM: Homo sapiens

<400> SEQUENCE: 22

Ile Tyr Ile Trp Ala Pro Leu Ala Gly Thr Cys Gly Val Leu Leu Leu
1               5                   10                  15

Ser Leu Val Ile Thr
            20
```

<210> SEQ ID NO 23
<211> LENGTH: 63
<212> TYPE: DNA
<213> ORGANISM: Homo sapiens

<400> SEQUENCE: 23
atctacatct gggcgcccit ggccgggact tgtggggtcc ttctcctgtc actggttatc     60
acc                                                                  63

<210> SEQ ID NO 24
<211> LENGTH: 55
<212> TYPE: PRT
<213> ORGANISM: Homo sapiens

<400> SEQUENCE: 24

Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
            20                  25                  30

Arg Pro Glu Ala Cys Arg Pro Ala Ala Gly Gly Ala Val His Thr Arg
        35                  40                  45

Gly Leu Asp Phe Ala Cys Asp
    50                  55

<210> SEQ ID NO 25
<211> LENGTH: 165
<212> TYPE: DNA
<213> ORGANISM: Homo sapiens

<400> SEQUENCE: 25
ttcgtgccgg tcttcctgcc agcgaagccc accacgacgc cagcgccgcg accaccaaca     60
ccggcgccca ccatcgcgtc gcagcccctg tccctgcgcc cagaggcgtg ccggccagca    120
gcaggaggag cagtgcacac gagggggctg gacttcgcct gtgat                    165

<210> SEQ ID NO 26
<211> LENGTH: 25
<212> TYPE: PRT
<213> ORGANISM: Homo sapiens

<400> SEQUENCE: 26

Met Ala Pro Ala Met Glu Ser Pro Thr Leu Leu Cys Val Ala Leu Leu
1               5                   10                  15

Phe Phe Ala Pro Asp Gly Val Leu Ala
            20                  25

<210> SEQ ID NO 27
<211> LENGTH: 75
<212> TYPE: DNA
<213> ORGANISM: Homo sapiens

<400> SEQUENCE: 27
atggctcctg ccatggaatc ccctactcta ctgtgtgtag ccttactgtt cttcgctcca     60
gatggcgtgt tagca                                                     75

<210> SEQ ID NO 28
<211> LENGTH: 22
<212> TYPE: PRT
<213> ORGANISM: Homo sapiens

<400> SEQUENCE: 28

Met Asp Phe Gln Val Gln Ile Phe Ser Phe Leu Leu Ile Ser Ala Ser
1               5                   10                  15

Val Ile Met Ser Arg Gly
            20

<210> SEQ ID NO 29
<211> LENGTH: 66
<212> TYPE: DNA
<213> ORGANISM: Homo sapiens

<400> SEQUENCE: 29
atggattttc aggtgcagat tttcagcttc ctgctaatca gtgcctcagt cataatgtcc    60
agagga                                                              66

<210> SEQ ID NO 30
<211> LENGTH: 1656
<212> TYPE: DNA
<213> ORGANISM: Artificial Sequence
<220> FEATURE:
<223> OTHER INFORMATION: Encoding synthesized EMPD-specific chimeric
      antigen receptor

<400> SEQUENCE: 30
atggattttc aggtgcagat tttcagcttc ctgctaatca gtgcctcagt cataatgtcc      60
agaggagatg ttgtgatgac ccagactcca ctcactttgt cggttaccat tggacaacca    120
gcctccatct cttgcaagtc aagtcagagc ctcttatata gtgatggaaa gacatatttg    180
aattggttgt tacagaggcc aggccagtct ccaaagcgcc taatctatct ggtgtctaaa    240
ctggactctg gagtccctga caggttcact ggcagtggat cagggacaga tttcacactg    300
aaaatcagca gagtggaggc tgaggatttg ggagtttatt attgctggca aggtacacat    360
tttcctcgga cgttcggtgg aggcaccaag ctggaaatca acggggggtc tacatctgga    420
tctgggaagc cgggttctgg tgagggttct gatgtgcagc ttcaggagtc aggacctggc    480
ctggtgaaac cttctcagtc tctgtccctc acctgcactg tcactggcta ctcaatcacc    540
agtgattatg cctggaactg gatccggcag tttccaagaa acaaactgga gtggatgggc    600
tacataagct acagtggtag gaatagctac aacccatctc tcaaaagtcg aatctctatc    660
actcgagaca catccaagaa ccagttcttc ctgcagttga attctgtgac tactgaggac    720
acagccacat attactgtgc aagatggggg gacttcgatg tctggggcgc agggaccacg    780
gtcaccgtct cctcagcggc cgcattcgtg ccggtcttcc tgccagcgaa gcccaccacg    840
acgccagcgc cgcgaccacc aacaccggcg cccaccatcg cgtcgcagcc cctgtccctg    900
cgcccagagg cgtgccggcc agcagcagga ggagcagtgc acacgagggg gctggacttc    960
gcctgtgata tctacatctg gcgcccttg gccgggactt gtggggtcct tctcctgtca   1020
ctggttatca ccctttactg caaccacagg aacaggagta gaggagcag gctcctgcac   1080
agtgactaca tgaacatgac tccccgccgc cccgggccca cccgcaagca ttaccagccc   1140
tatgccccac cacgcgactt cgcagcctat cgctcccgtt tctctgttgt taaacggggc   1200
agaaagaagc tcctgtatat attcaaacaa ccatttatga ccagtacaa aactactcaa   1260
gaggaagatg gctgtagctg ccgatttcca gaagaagaag aaggaggatg tgaactgaga   1320
gtgaagttca gcaggagcgc agacgccccc gcgtaccagc agggccagaa ccagctctat   1380
aacgagctca atctaggacg aagagaggag tacgatgttt tggacaagag acgtggccgg   1440

```
gaccctgaga tgggggggaaa gccgcagaga aggaagaacc ctcaggaagg cctgtacaat    1500
gaactgcaga aagataagat ggcggaggcc tacagtgaga ttgggatgaa aggcgagcgc    1560 cggagggggca aggggcacga tggcctttac cagggtctca gtacagccac caaggacacc    1620
tacgacgccc ttcacatgca ggccctgccc cctcgc                              1656
```

<210> SEQ ID NO 31
<211> LENGTH: 552
<212> TYPE: PRT
<213> ORGANISM: Artificial Sequence
<220> FEATURE:
<223> OTHER INFORMATION: Synthesized EMPD-specific chimeric antigen
    receptor

<400> SEQUENCE: 31

```
Met Asp Phe Gln Val Gln Ile Phe Ser Phe Leu Leu Ile Ser Ala Ser
1               5                   10                  15

Val Ile Met Ser Arg Gly Asp Val Val Met Thr Gln Thr Pro Leu Thr
            20                  25                  30

Leu Ser Val Thr Ile Gly Gln Pro Ala Ser Ile Ser Cys Lys Ser Ser
        35                  40                  45

Gln Ser Leu Leu Tyr Ser Asp Gly Lys Thr Tyr Leu Asn Trp Leu Leu
    50                  55                  60

Gln Arg Pro Gly Gln Ser Pro Lys Arg Leu Ile Tyr Leu Val Ser Lys
65                  70                  75                  80

Leu Asp Ser Gly Val Pro Asp Arg Phe Thr Gly Ser Gly Ser Gly Thr
                85                  90                  95

Asp Phe Thr Leu Lys Ile Ser Arg Val Glu Ala Glu Asp Leu Gly Val
            100                 105                 110

Tyr Tyr Cys Trp Gln Gly Thr His Phe Pro Arg Thr Phe Gly Gly Gly
        115                 120                 125

Thr Lys Leu Glu Ile Lys Arg Gly Ser Thr Ser Gly Ser Gly Lys Pro
    130                 135                 140

Gly Ser Gly Glu Gly Ser Asp Val Gln Leu Gln Glu Ser Gly Pro Gly
145                 150                 155                 160

Leu Val Lys Pro Ser Gln Ser Leu Ser Leu Thr Cys Thr Val Thr Gly
                165                 170                 175

Tyr Ser Ile Thr Ser Asp Tyr Ala Trp Asn Trp Ile Arg Gln Phe Pro
            180                 185                 190

Arg Asn Lys Leu Glu Trp Met Gly Tyr Ile Ser Tyr Ser Gly Arg Asn
        195                 200                 205

Ser Tyr Asn Pro Ser Leu Lys Ser Arg Ile Ser Ile Thr Arg Asp Thr
    210                 215                 220

Ser Lys Asn Gln Phe Phe Leu Gln Leu Asn Ser Val Thr Thr Glu Asp
225                 230                 235                 240

Thr Ala Thr Tyr Tyr Cys Ala Arg Trp Gly Asp Phe Asp Val Trp Gly
                245                 250                 255

Ala Gly Thr Thr Val Thr Val Ser Ser Ala Ala Ala Phe Val Pro Val
            260                 265                 270

Phe Leu Pro Ala Lys Pro Thr Thr Thr Pro Ala Pro Arg Pro Pro Thr
        275                 280                 285

Pro Ala Pro Thr Ile Ala Ser Gln Pro Leu Ser Leu Arg Pro Glu Ala
    290                 295                 300

Cys Arg Pro Ala Ala Gly Gly Ala Val His Thr Arg Gly Leu Asp Phe
305                 310                 315                 320
```

```
Ala Cys Asp Ile Tyr Ile Trp Ala Pro Leu Ala Gly Thr Cys Gly Val
            325                 330                 335

Leu Leu Leu Ser Leu Val Ile Thr Leu Tyr Cys Asn His Arg Asn Arg
            340                 345                 350

Ser Lys Arg Ser Arg Leu Leu His Ser Asp Tyr Met Asn Met Thr Pro
            355                 360                 365

Arg Arg Pro Gly Pro Thr Arg Lys His Tyr Gln Pro Tyr Ala Pro Pro
            370                 375                 380

Arg Asp Phe Ala Ala Tyr Arg Ser Arg Phe Ser Val Val Lys Arg Gly
385                 390                 395                 400

Arg Lys Lys Leu Leu Tyr Ile Phe Lys Gln Pro Phe Met Arg Pro Val
            405                 410                 415

Gln Thr Thr Gln Glu Glu Asp Gly Cys Ser Cys Arg Phe Pro Glu Glu
            420                 425                 430

Glu Glu Gly Gly Cys Glu Leu Arg Val Lys Phe Ser Arg Ser Ala Asp
            435                 440                 445

Ala Pro Ala Tyr Gln Gln Gly Gln Asn Gln Leu Tyr Asn Glu Leu Asn
            450                 455                 460

Leu Gly Arg Arg Glu Glu Tyr Asp Val Leu Asp Lys Arg Arg Gly Arg
465                 470                 475                 480

Asp Pro Glu Met Gly Gly Lys Pro Arg Arg Lys Asn Pro Gln Glu
            485                 490                 495

Gly Leu Tyr Asn Glu Leu Gln Lys Asp Lys Met Ala Glu Ala Tyr Ser
            500                 505                 510

Glu Ile Gly Met Lys Gly Glu Arg Arg Arg Gly Lys Gly His Asp Gly
            515                 520                 525

Leu Tyr Gln Gly Leu Ser Thr Ala Thr Lys Asp Thr Tyr Asp Ala Leu
            530                 535                 540

His Met Gln Ala Leu Pro Pro Arg
545                 550

<210> SEQ ID NO 32
<211> LENGTH: 12
<212> TYPE: PRT
<213> ORGANISM: Mus musculus

<400> SEQUENCE: 32

Gln Ser Leu Leu Tyr Ser Ser Asn Gln Lys Asn Tyr
1               5                   10

<210> SEQ ID NO 33
<211> LENGTH: 9
<212> TYPE: PRT
<213> ORGANISM: Mus musculus

<400> SEQUENCE: 33

Gln Gln Tyr Tyr Ser Tyr Pro Tyr Thr
1               5

<210> SEQ ID NO 34
<211> LENGTH: 8
<212> TYPE: PRT
<213> ORGANISM: Mus musculus

<400> SEQUENCE: 34

Gly Tyr Ser Phe Thr Ser His Trp
1               5
```

```
<210> SEQ ID NO 35
<211> LENGTH: 8
<212> TYPE: PRT
<213> ORGANISM: Mus musculus

<400> SEQUENCE: 35

Ile Tyr Pro Gly Asn Ser Asp Thr
1               5

<210> SEQ ID NO 36
<211> LENGTH: 14
<212> TYPE: PRT
<213> ORGANISM: Mus musculus

<400> SEQUENCE: 36

Thr Arg Trp Arg Asp Asn Tyr Asp Tyr Asp Met Asp Tyr
1               5                   10

<210> SEQ ID NO 37
<211> LENGTH: 12
<212> TYPE: PRT
<213> ORGANISM: Mus musculus

<400> SEQUENCE: 37

Gln Ser Leu Leu Tyr Ser Ser Asn Gln Lys Asn Tyr
1               5                   10

<210> SEQ ID NO 38
<211> LENGTH: 9
<212> TYPE: PRT
<213> ORGANISM: Mus musculus

<400> SEQUENCE: 38

Gln Gln Tyr Tyr Ser Tyr Pro Trp Thr
1               5

<210> SEQ ID NO 39
<211> LENGTH: 9
<212> TYPE: PRT
<213> ORGANISM: Mus musculus

<400> SEQUENCE: 39

Gly Tyr Ser Ile Thr Ser Gly Tyr Tyr
1               5

<210> SEQ ID NO 40
<211> LENGTH: 7
<212> TYPE: PRT
<213> ORGANISM: Mus musculus

<400> SEQUENCE: 40

Ile Ser Tyr Asp Gly Ser Asn
1               5

<210> SEQ ID NO 41
<211> LENGTH: 9
<212> TYPE: PRT
<213> ORGANISM: Mus musculus

<400> SEQUENCE: 41

Ala Arg Asp Tyr Gly Gly Phe Asp Tyr
1               5
```

<210> SEQ ID NO 42
<211> LENGTH: 12
<212> TYPE: PRT
<213> ORGANISM: Mus musculus

<400> SEQUENCE: 42

Gln Ser Leu Leu Tyr Ser Asp Gly Lys Thr Tyr Leu
1               5                   10

<210> SEQ ID NO 43
<211> LENGTH: 9
<212> TYPE: PRT
<213> ORGANISM: Mus musculus

<400> SEQUENCE: 43

Trp Gln Gly Thr His Phe Pro Arg Thr
1               5

<210> SEQ ID NO 44
<211> LENGTH: 9
<212> TYPE: PRT
<213> ORGANISM: Mus musculus

<400> SEQUENCE: 44

Gly Tyr Ser Ile Thr Ser Asp Tyr Ala
1               5

<210> SEQ ID NO 45
<211> LENGTH: 7
<212> TYPE: PRT
<213> ORGANISM: Mus musculus

<400> SEQUENCE: 45

Ile Ser Tyr Ser Gly Arg Asn
1               5

<210> SEQ ID NO 46
<211> LENGTH: 8
<212> TYPE: PRT
<213> ORGANISM: Mus musculus

<400> SEQUENCE: 46

Ala Arg Trp Gly Asp Phe Asp Val
1               5

<210> SEQ ID NO 47
<211> LENGTH: 336
<212> TYPE: DNA
<213> ORGANISM: Homo sapiens

<400> SEQUENCE: 47
gtgaagttca gcaggagcgc agacgccccc gcgtaccagc agggccagaa ccagctctat        60
aacgagctca atctaggacg aagagaggag tacgatgttt tggacaagag acgtggccgg       120
gaccctgaga tgggggggaaa gccgcagaga aggaagaacc ctcaggaagg cctgtacaat      180
gaactgcaga agataagat ggcggaggcc tacagtgaga ttgggatgaa aggcgagcgc        240
cggaggggca aggggcacga tggcctttac cagggtctca gtacagccac caaggacacc      300
tacgacgccc ttcacatgca ggccctgccc cctcgc                                 336

<210> SEQ ID NO 48
<211> LENGTH: 89
<212> TYPE: PRT
<213> ORGANISM: Artificial Sequence
<220> FEATURE:
<223> OTHER INFORMATION: Synthesized; fusion polypeptide derived from
     human CD28 and 4-1BB

<400> SEQUENCE: 48

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
                20                  25                  30

Pro Arg Asp Phe Ala Ala Tyr Arg Ser Arg Phe Ser Val Val Lys Arg
            35                  40                  45

Gly Arg Lys Lys Leu Leu Tyr Ile Phe Lys Gln Pro Phe Met Arg Pro
    50                  55                  60

Val Gln Thr Thr Gln Glu Asp Gly Cys Ser Cys Arg Phe Pro Glu
65                  70                  75                  80

Glu Glu Glu Gly Gly Cys Glu Leu Arg
                85

<210> SEQ ID NO 49
<211> LENGTH: 267
<212> TYPE: DNA
<213> ORGANISM: Artificial Sequence
<220> FEATURE:
<223> OTHER INFORMATION: Encoding synthesized fusion polypeptide derived
     from human CD28 and 4-1BB

<400> SEQUENCE: 49
aggagtaaga ggagcaggct cctgcacagt gactacatga acatgactcc ccgccgcccc      60
gggcccaccc gcaagcatta ccagccctat gccccaccac gcgacttcgc agcctatcgc     120
tcccgtttct ctgttgttaa acggggcaga agaagctcc tgtatatatt caaacaacca      180
tttatgagac cagtacaaac tactcaagag gaagatggct gtagctgccg atttccagaa     240
gaagaagaag aggatgtgaa actgaga                                         267

<210> SEQ ID NO 50
<211> LENGTH: 48
<212> TYPE: PRT
<213> ORGANISM: Homo sapiens

<400> SEQUENCE: 50

Arg Phe Ser Val Val Lys Arg Gly Arg Lys Lys Leu Leu Tyr Ile Phe
1               5                   10                  15

Lys Gln Pro Phe Met Arg Pro Val Gln Thr Thr Gln Glu Glu Asp Gly
                20                  25                  30

Cys Ser Cys Arg Phe Pro Glu Glu Glu Glu Gly Gly Cys Glu Leu Arg
            35                  40                  45

<210> SEQ ID NO 51
<211> LENGTH: 144
<212> TYPE: DNA
<213> ORGANISM: Homo sapiens

<400> SEQUENCE: 51
cgtttctctg ttgttaaacg gggcagaaag aaactcctgt atatattcaa acaaccattt      60
atgagaccag tacaaactac tcaagaggaa gatggctgta gctgccgatt ccagaagaa      120 gaagaaggag gatgtgaact gaga                                            144